US011118238B2

(12) United States Patent
Murillo Sauca et al.

(10) Patent No.: US 11,118,238 B2
(45) Date of Patent: *Sep. 14, 2021

(54) NUCLEIC ACID CONSTRUCTS AND GENE THERAPY VECTORS FOR USE IN THE TREATMENT OF WILSON'S DISEASE AND OTHER CONDITIONS

(71) Applicant: FUNDACIÓN PARA LA INVESTIGACIÓN MÈDICA APLICADA, Pamplona (ES)

(72) Inventors: Oihana Murillo Sauca, Pamplona (ES); Gloria González Aseguinolaza, Pamplona (ES); Rubén Hernández Alcoceba, Pamplona (ES)

(73) Assignee: FUNDACIÓN PARA LA INVESTIGACIÓN MÈDICA APLICADA, Pamplona (ES)

( * ) Notice: Subject to any disclaimer, the term of this patent is extended or adjusted under 35 U.S.C. 154(b) by 809 days.

This patent is subject to a terminal disclaimer.

(21) Appl. No.: 15/537,801

(22) PCT Filed: Dec. 17, 2015

(86) PCT No.: PCT/EP2015/080356
§ 371 (c)(1),
(2) Date: Jun. 19, 2017

(87) PCT Pub. No.: WO2016/097218
PCT Pub. Date: Jun. 23, 2016

(65) Prior Publication Data
US 2017/0356060 A1    Dec. 14, 2017

(30) Foreign Application Priority Data
Dec. 17, 2014   (EP) ..................... 14382530

(51) Int. Cl.
*A61K 48/00*  (2006.01)
*C12N 9/14*   (2006.01)
(52) U.S. Cl.
CPC .... *C12Y 306/03004* (2013.01); *A61K 48/005* (2013.01); *A61K 48/0058* (2013.01); *C12N 9/14* (2013.01); *C12N 2750/14143* (2013.01); *C12N 2800/22* (2013.01); *C12N 2830/008* (2013.01); *C12N 2830/85* (2013.01)
(58) Field of Classification Search
CPC ... A61K 47/6455; A61K 47/545; A61P 25/28; C07K 5/1016; C07K 5/1019; C07K 7/66
See application file for complete search history.

(56) References Cited
U.S. PATENT DOCUMENTS
2013/0158104 A1* 6/2013 Tubert ............... A61K 48/0066
514/44 R

FOREIGN PATENT DOCUMENTS

| DE | 101 56 121 A1 | 5/2003 | |
| DE | 10156121 A1 * | 5/2003 | ............. C12N 15/86 |
| JP | H10-146191 A | 6/1998 | |
| WO | 01/45510 A1 | 6/2001 | |
| WO | WO-2013151666 A2 * | 10/2013 | ............... A61P 1/00 |
| WO | 2016/097218 A1 | 6/2016 | |

OTHER PUBLICATIONS

Roybal et al.; Early gestational gene transfer with targeted ATP7B expression in the liver improves phenotype in a murine model of Wilson's disease; Gene Therapy; vol. 19, No. 11, pp. 1085-1094, published Dec. 2011 (Year: 2011).*
Wu et al.; Adeno-associated Virus Serotypes: Vector Toolkit for Human Gene Therapy; Molecular Therapy; vol. 14, No. 3, pp. 316-327, published Aug. 2006 (Year: 2006).*
DE10156121A1 translation, pp. 1-6, accessed Apr. 13, 2020 (Year: 2020).*
Khan et al.; AAV-mediated gene targeting methods for human cells; Nature Protocols; vol. 6, No. 4, pp. 482-501, published online Mar. 24, 2011 (Year: 2011).*
Stratagene (1988 catalog, Gene Characterization Kits, p. 39 (Year: 1988).*
Mar. 11, 2016 Written Opinion issued in International Patent Application No. PCT/EP2015/080357.
Mar. 11, 2016 International Search Report issued in International Patent Application No. PCT/EP2015/080357.
Huster, Dominik, et al. "The Distinct Roles of the N-Terminal Copper-Binding Sites in Regulation of Catalytic Activity of the Wilson's Disease Protein". The Journal of Biological Chemistry, vol. 278, No. 34, pp. 32212-32218, 2003.
Roybal, J.L., et al. "Early Gestational Gene Transfer With Targeted ATP7B Expression in the Liver Improves Phenotype in a Murine Model of Wilson's Disease". Gene Therapy, vol. 19, pp. 1085-1094, 2012.
Wu, Zhijian, et al. "Adeno-Associated Virus Serotypes: Vector Toolkit for Human Gene Therapy". Molecular Therapy, vol. 14, No. 3, 2006.
Hu, Huimin, et al. "Preclinical Dose-Finding Study With a Liver-Tropic, Recombinant AAV-2/8 Vector in the Mouse Model of Galactosialidosis". Molecular Therapy, vol. 20, No. 2, pp. 267-274, 2012.
Pilankatta, Rajendra, et al. "Functional Effects of N-Metal Binding Domain Deletion and Specific Mutations on the ATP7B (Wilson Disease) Copper ATPase". Biophysical Journal, vol. 98, No. 3, pp. 448a, 2010.

(Continued)

*Primary Examiner* — Antonio Galisteo Gonzalez
(74) *Attorney, Agent, or Firm* — Oliff PLC

(57) ABSTRACT

The invention relates to a nucleic acid construct carrying ATP7B protein, an expression vector and a viral particle comprising the nucleic acid construct, and their use for treatment of Wilson's disease and other conditions caused by a deficiency or dysfunction of ATP7B protein. An AAV vector devised according to the invention significantly reduced urine Cu excretion, and liver Cu content in Wilson's disease mice treated with the vector, while ceruloplasmin activity was significantly restored. On the other hand, the administration of the vector resulted in the normalization of serum transaminases levels and of liver histology, together with a marked reduction of the inflammatory infiltrate.

Figure 1:
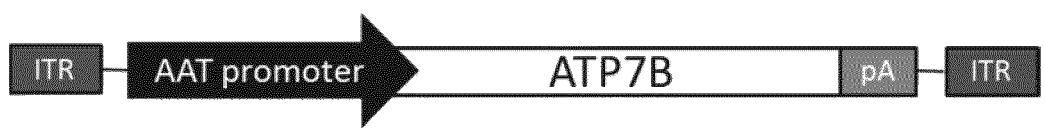

24 Claims, 8 Drawing Sheets
Specification includes a Sequence Listing.

(56) References Cited

OTHER PUBLICATIONS

Forbes, John R., et al. "Role of the Copper-Binding Domain in the Copper Transport Function of ATP7B, The P-Type ATPase Defective in Wilson Disease". The Journal of Biological Chemistry, vol. 274, No. 18, pp. 12408-12413, 1999.
Portmann, Reto, et al. "Purification and Functional Reconstitution of the Human Wilson Copper ATPase, ATP7B". FEBS Letter, vol. 579, pp. 3589-3595, 2005.
Lorinczi, Eva, et al. "Delivery of the Cu-Transporting ATPase ATP7B to the Plasma Membrane in Xenopus Oocytes". Biochim Biophys Acta, vol. 1778, No. 4, pp. 896-906, 2008.
Murillo, Oihana, et al. "Long-Term Metabolic Correction of Wilson's Disease in a Murine Model By Gene Therapy." Journal of Hepatology, vol. 64, pp. 419-426, 2016.
Margaritis, Paris, et al. "Novel Therapeutic Approach for Hemophilia Using Gene Delivery of an Engineered Secreted Activated Factor VII". The Journal of Clinical Investigation, vol. 113, No. 7, pp. 1025-1031, 2004.
Unzu, C., et al. "AAV Mediated Liver Gene Therapy Provides Prolonged Enzymatic Correction and Protects Against Induced Motor Neuropathy in Acute Intermittent Porphyria Mice". Journal of Hepatology, vol. 52, pp. S437-S438, 2010.
Sep. 17, 2019 Office Action issued in U.S. Appl. No. 15/537,781.
Ling, Chen et al., "Human Hepatocyte Growth Factor Receptor Is a Cellular Coreceptor for Adeno-Associated Virus Serotype 3", Human Gene Therapy, vol. 21, (2010), pp. 1741-1747.
Apr. 4, 2016 Written Opinion of the International Searching Authority issued in International Patent Application No. PCT/EP2015/080356.
Apr. 4, 2016 International Search Report issued in International Patent Application No. PCT/EP2015/080356.
Jan. 31, 2020 Office Action issued in U.S. Appl. No. 15/537,781.
Jun. 26, 2020 Office Action issued in U.S. Appl. No. 15/537,781.
Dec. 15, 2020 Office Action issued in U.S. Appl. No. 15/537,781.
Lutsenko et al. "Biochemical Basis of Regulation of Human Copper-Transporting ATPases" Arch Biochem Biophys., 463(2), 2007, pp. 134-148.
Apr. 4, 2016 International Search Report issued in International Application No. PCT/EP2015/080356.
Klyaritskaya et al. "Wilson's Disease: Clinical Guidelines for Diagnosis and Treatment" Crimean Thera. J , vol. 19, No. 2, pp. 51-57, 2012.
Ha-Hao, D. et al. "Chances and Shortcomings of Adenovirus-Mediated ATP7B Gene Transfer in Wilson Disease Proof of Principle Demonstrated in a Pilot Study with LEG Rats" Z Gastroenterol, vol. 40, pp. 209-216, 2002.
Terada, K. et al. "Restoration of Holoceruloplasmin Synthesis in LEC Rat After Infusion of Recombinant Adenovirus Bearing WND cDNA" The Journal of Biological Chemistry, vol. 273, No. 3, pp. 1815-1820, 1998.
Terada, K. et al. "Biliary Excretion of Copper in LEC Rat After Introduction of Copper Transporting p. Type ATPase, ATP7B" Federation of European Biochemical Societies Letters, vol. 448, pp. 53-56, 1999.
Kramer, M. G. et al. "In Vitro and In Vivo Comparative Study in Chimeric Liver-Specific Promoters" Molecular Therapy, vol. 7, No. 3, pp. 375-385, 2003.
De Simone, V. et al. "Cis- and Trans-Acting Elements Responsible for the Cell-Specific Expression of the Human $\alpha$1-Antitrypsin Gene" The EMBO Journal, vol. 6, No. 9, pp. 2759-2766, 1987.
Manno, C. S et al. "Successful Transduction of Liver in Hemophilia by AAV-Factor IX and Limitations Imposed by the Host Immune Response" Nature Medicine, vol. 12, No. 3, pp. 342-347, 2006 (with Errata and Corrigenda: vol. 12, No. 5, p. 592, 2006).
Murillo, O. et al. "Liver Expression of a MiniATP7B Gene Results in Long-Term Restoration of Copper Homeostasis n a Wilson Disease Model in Mice" Hepatology, vol. 70, No. 1, pp. 108-126, 2019.
GenBank NCBI accession No. NM_000053, 2014, <https://www.ncbi.nlm.nih.gov/clinvar/RCV000004070/>.
Merle, U. et al. "Lentiviral Gene Transfer Ameliorates Disease Progression in Long-Evans Cinnamon Rats: An Animal Model for Wilson Disease" Scandinavian Journal of Gastroenterology, vol. 41, pp. 974-982, 2006.
Merle, U. et al. "Perspectives for Gene Therapy of Wilson Disease" Current Gene Therapy, vol. 7, No. 3, pp. 217-220, 2007.
Apr. 4, 2016 Written Opinion of the International Searching Authority issued in International Application No. PCT/EP2015/080356.

* cited by examiner

SEQUENCE LISTING

```
<160> NUMBER OF SEQ ID NOS: 6

<210> SEQ ID NO 1
<211> LENGTH: 5107
<212> TYPE: DNA
<213> ORGANISM: Artificial Sequence
<220> FEATURE:
<223> OTHER INFORMATION: Nucleic acid construct of expression vector
      AAV2-AAT-wtATP7B
<220> FEATURE:
<221> NAME/KEY: repeat_region
<222> LOCATION: 1..141
<223> OTHER INFORMATION: /note="5' ITR of adeno-associated virus
      serotype 2"
<220> FEATURE:
<221> NAME/KEY: promoter
<222> LOCATION: 156..460
<223> OTHER INFORMATION: /note="alpha 1 antitrypsin"
<220> FEATURE:
<221> NAME/KEY: CDS
<222> LOCATION: 473..4870
<223> OTHER INFORMATION: /note="Sequence encoding ATP7B (Copper
      transporting ATPase 2)" /transl_table=1
<220> FEATURE:
<221> NAME/KEY: polyA_signal
<222> LOCATION: 4877..4932
<220> FEATURE:
<221> NAME/KEY: repeat_region
<222> LOCATION: 4968..5107
<223> OTHER INFORMATION: /standard_name="3' ITR of adeno-associated
      virus serotype 2"

<400> SEQUENCE: 1
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtcgcca cccctccac cttgacaca      180 ggacgctgtg gtttctgagc caggtacaat gactcctttc ggtaagtgca gtggaagctg     240
```

```
tacactgccc aggcaaagcg tccgggcagc gtaggcgggc gactcagatc ccagccagtg    300
gacttagccc ctgtttgctc ctccgataac tggggtgacc ttggttaata ttcaccagca    360
gcctcccccg ttgcccctct ggatccactg cttaaatacg gacgaggaca gggccctgtc    420
tcctcagctt caggcaccac cactgacctg gacagtgaa gcggccgcca cc atg cct    478
                                                          Met Pro
                                                           1
```

| | | |
|---|---|---|
| gag cag gag aga cag atc aca gcc aga gaa ggg gcc agt cgg aaa atc<br>Glu Gln Glu Arg Gln Ile Thr Ala Arg Glu Gly Ala Ser Arg Lys Ile<br>     5               10              15 | | 526 |
| tta tct aag ctt tct ttg cct acc cgt gcc tgg gaa cca gca atg aag<br>Leu Ser Lys Leu Ser Leu Pro Thr Arg Ala Trp Glu Pro Ala Met Lys<br>   20             25             30 | | 574 |
| aag agt ttt gct ttt gac aat gtt ggc tat gaa ggt ggt ctg gat ggc<br>Lys Ser Phe Ala Phe Asp Asn Val Gly Tyr Glu Gly Gly Leu Asp Gly<br>35           40             45            50 | | 622 |
| ctg ggc cct tct tct cag gtg gcc acc agc aca gtc agg atc ttg ggc<br>Leu Gly Pro Ser Ser Gln Val Ala Thr Ser Thr Val Arg Ile Leu Gly<br>              55            60           65 | | 670 |
| atg act tgc cag tca tgt gtg aag tcc att gag gac agg att tcc aat<br>Met Thr Cys Gln Ser Cys Val Lys Ser Ile Glu Asp Arg Ile Ser Asn<br>         70             75             80 | | 718 |
| ttg aaa ggc atc atc agc atg aag gtt tcc ctg gaa caa ggc agt gcc<br>Leu Lys Gly Ile Ile Ser Met Lys Val Ser Leu Glu Gln Gly Ser Ala<br>              85            90           95 | | 766 |
| act gtg aaa tat gtg cca tcg gtt gtg tgc ctg caa cag gtt tgc cat<br>Thr Val Lys Tyr Val Pro Ser Val Val Cys Leu Gln Gln Val Cys His<br>    100             105            110 | | 814 |
| caa att ggg gac atg ggc ttc gag gcc agc att gca gaa gga aag gca<br>Gln Ile Gly Asp Met Gly Phe Glu Ala Ser Ile Ala Glu Gly Lys Ala<br>115             120            125           130 | | 862 |
| gcc tcc tgg ccc tca agg tcc ttg cct gcc cag gag gct gtg gtc aag<br>Ala Ser Trp Pro Ser Arg Ser Leu Pro Ala Gln Glu Ala Val Val Lys<br>               135            140           145 | | 910 |
| ctc cgg gtg gag ggc atg acc tgc cag tcc tgt gtc agc tcc att gaa<br>Leu Arg Val Glu Gly Met Thr Cys Gln Ser Cys Val Ser Ser Ile Glu<br>          150             155            160 | | 958 |
| ggc aag gtc cgg aaa ctg caa gga gta gtg aga gtc aaa gtc tca ctc<br>Gly Lys Val Arg Lys Leu Gln Gly Val Val Arg Val Lys Val Ser Leu<br>             165            170           175 | | 1006 |
| agc aac caa gag gcc gtc atc act tat cag cct tat ctc att cag ccc<br>Ser Asn Gln Glu Ala Val Ile Thr Tyr Gln Pro Tyr Leu Ile Gln Pro<br>        180             185            190 | | 1054 |
| gaa gac ctc agg gac cat gta aat gac atg gga ttt gaa gct gcc atc<br>Glu Asp Leu Arg Asp His Val Asn Asp Met Gly Phe Glu Ala Ala Ile<br>195             200            205           210 | | 1102 |
| aag agc aaa gtg gct ccc tta agc ctg gga cca att gat att gag cgg<br>Lys Ser Lys Val Ala Pro Leu Ser Leu Gly Pro Ile Asp Ile Glu Arg<br>               215            220           225 | | 1150 |
| tta caa agc act aac cca aag aga cct tta tct tct gct aac cag aat<br>Leu Gln Ser Thr Asn Pro Lys Arg Pro Leu Ser Ser Ala Asn Gln Asn<br>        230             235            240 | | 1198 |
| ttt aat aat tct gag acc ttg ggg cac caa gga agc cat gtg gtc acc<br>Phe Asn Asn Ser Glu Thr Leu Gly His Gln Gly Ser His Val Val Thr<br>          245             250            255 | | 1246 |
| ctc caa ctg aga ata gat gga atg cat tgt aag tct tgc gtc ttg aat<br>Leu Gln Leu Arg Ile Asp Gly Met His Cys Lys Ser Cys Val Leu Asn<br>        260             265            270 | | 1294 |

|   |   |
|---|---|
| att gaa gaa aat att ggc cag ctc cta ggg gtt caa agt att caa gtg<br>Ile Glu Glu Asn Ile Gly Gln Leu Leu Gly Val Gln Ser Ile Gln Val<br>275                        280                     285                     290 | 1342 |
| tcc ttg gag aac aaa act gcc caa gta aag tat gac cct tct tgt acc<br>Ser Leu Glu Asn Lys Thr Ala Gln Val Lys Tyr Asp Pro Ser Cys Thr<br>                     295                     300                     305 | 1390 |
| agc cca gtg gct ctg cag agg gct atc gag gca ctt cca cct ggg aat<br>Ser Pro Val Ala Leu Gln Arg Ala Ile Glu Ala Leu Pro Pro Gly Asn<br>310                     315                     320 | 1438 |
| ttt aaa gtt tct ctt cct gat gga gcc gaa ggg agt ggg aca gat cac<br>Phe Lys Val Ser Leu Pro Asp Gly Ala Glu Gly Ser Gly Thr Asp His<br>               325                     330                     335 | 1486 |
| agg tct tcc agt tct cat tcc cct ggc tcc cca ccg aga aac cag gtc<br>Arg Ser Ser Ser Ser His Ser Pro Gly Ser Pro Pro Arg Asn Gln Val<br>340                     345                     350 | 1534 |
| cag ggc aca tgc agt acc act ctg att gcc att gcc ggc atg acc tgt<br>Gln Gly Thr Cys Ser Thr Thr Leu Ile Ala Ile Ala Gly Met Thr Cys<br>355                     360                     365                     370 | 1582 |
| gca tcc tgt gtc cat tcc att gaa ggc atg atc tcc caa ctg gaa ggg<br>Ala Ser Cys Val His Ser Ile Glu Gly Met Ile Ser Gln Leu Glu Gly<br>                     375                     380                     385 | 1630 |
| gtg cag caa ata tcg gtg tct ttg gcc gaa ggg act gca aca gtt ctt<br>Val Gln Gln Ile Ser Val Ser Leu Ala Glu Gly Thr Ala Thr Val Leu<br>               390                     395                     400 | 1678 |
| tat aat ccc tct gta att agc cca gaa gaa ctc aga gct gct ata gaa<br>Tyr Asn Pro Ser Val Ile Ser Pro Glu Glu Leu Arg Ala Ala Ile Glu<br>                     405                     410                     415 | 1726 |
| gac atg gga ttt gag gct tca gtc gtt tct gaa agc tgt tct act aac<br>Asp Met Gly Phe Glu Ala Ser Val Val Ser Glu Ser Cys Ser Thr Asn<br>420                     425                     430 | 1774 |
| cct ctt gga aac cac agt gct ggg aat tcc atg gtg caa act aca gat<br>Pro Leu Gly Asn His Ser Ala Gly Asn Ser Met Val Gln Thr Thr Asp<br>435                     440                     445                     450 | 1822 |
| ggt aca cct aca tct gtg cag gaa gtg gct ccc cac act ggg agg ctc<br>Gly Thr Pro Thr Ser Val Gln Glu Val Ala Pro His Thr Gly Arg Leu<br>                     455                     460                     465 | 1870 |
| cct gca aac cat gcc ccg gac atc ttg gca aag tcc cca caa tca acc<br>Pro Ala Asn His Ala Pro Asp Ile Leu Ala Lys Ser Pro Gln Ser Thr<br>               470                     475                     480 | 1918 |
| aga gca gtg gca ccg cag aag tgc ttc tta cag atc aaa ggc atg acc<br>Arg Ala Val Ala Pro Gln Lys Cys Phe Leu Gln Ile Lys Gly Met Thr<br>485                     490                     495 | 1966 |
| tgt gca tcc tgt gtg tct aac ata gaa agg aat ctg cag aaa gaa gct<br>Cys Ala Ser Cys Val Ser Asn Ile Glu Arg Asn Leu Gln Lys Glu Ala<br>500                     505                     510 | 2014 |
| ggt gtt ctc tcc gtg ttg gtt gcc ttg atg gca gga aag gca gag atc<br>Gly Val Leu Ser Val Leu Val Ala Leu Met Ala Gly Lys Ala Glu Ile<br>515                     520                     525                     530 | 2062 |
| aag tat gac cca gag gtc atc cag ccc ctc gag ata gct cag ttc atc<br>Lys Tyr Asp Pro Glu Val Ile Gln Pro Leu Glu Ile Ala Gln Phe Ile<br>                     535                     540                     545 | 2110 |
| cag gac ctg ggt ttt gag gca gca gtc atg gag gac tac gca ggc tcc<br>Gln Asp Leu Gly Phe Glu Ala Ala Val Met Glu Asp Tyr Ala Gly Ser<br>               550                     555                     560 | 2158 |
| gat ggc aac att gag ctg aca atc aca ggg atg acc tgc gcg tcc tgt<br>Asp Gly Asn Ile Glu Leu Thr Ile Thr Gly Met Thr Cys Ala Ser Cys<br>               565                     570                     575 | 2206 |
| gtc cac aac ata gag tcc aaa ctc acg agg aca aat ggc atc act tat<br>Val His Asn Ile Glu Ser Lys Leu Thr Arg Thr Asn Gly Ile Thr Tyr<br>580                     585                     590 | 2254 |

```
gcc tcc gtt gcc ctt gcc acc agc aaa gcc ctt gtt aag ttt gac ccg   2302
Ala Ser Val Ala Leu Ala Thr Ser Lys Ala Leu Val Lys Phe Asp Pro
595                 600                 605                 610 gaa att atc ggt cca cgg gat att atc aaa att att gag gaa att ggc   2350
Glu Ile Ile Gly Pro Arg Asp Ile Ile Lys Ile Ile Glu Glu Ile Gly
            615                 620                 625 ttt cat gct tcc ctg gcc cag aga aac ccc aac gct cat cac ttg gac   2398
Phe His Ala Ser Leu Ala Gln Arg Asn Pro Asn Ala His His Leu Asp
        630                 635                 640 cac aag atg gaa ata aag cag tgg aag aag tct ttc ctg tgc agc ctg   2446
His Lys Met Glu Ile Lys Gln Trp Lys Lys Ser Phe Leu Cys Ser Leu
    645                 650                 655 gtg ttt ggc atc cct gtc atg gcc tta atg atc tat atg ctg ata ccc   2494
Val Phe Gly Ile Pro Val Met Ala Leu Met Ile Tyr Met Leu Ile Pro
660                 665                 670 agc aac gag ccc cac cag tcc atg gtc ctg gac cac aac atc att cca   2542
Ser Asn Glu Pro His Gln Ser Met Val Leu Asp His Asn Ile Ile Pro
675                 680                 685                 690 gga ctg tcc att cta aat ctc atc ttc ttt atc ttg tgt acc ttt gtc   2590
Gly Leu Ser Ile Leu Asn Leu Ile Phe Phe Ile Leu Cys Thr Phe Val
            695                 700                 705 cag ctc ctc ggt ggg tgg tac ttc tac gtt cag gcc tac aaa tct ctg   2638
Gln Leu Leu Gly Gly Trp Tyr Phe Tyr Val Gln Ala Tyr Lys Ser Leu
        710                 715                 720 aga cac agg tca gcc aac atg gac gtg ctc atc gtc ctg gcc aca agc   2686
Arg His Arg Ser Ala Asn Met Asp Val Leu Ile Val Leu Ala Thr Ser
    725                 730                 735 att gct tat gtt tat tct ctg gtc atc ctg gtg gtt gct gtg gct gag   2734
Ile Ala Tyr Val Tyr Ser Leu Val Ile Leu Val Val Ala Val Ala Glu
740                 745                 750 aag gcg gag agg agc cct gtg aca ttc ttc gac acg ccc ccc atg ctc   2782
Lys Ala Glu Arg Ser Pro Val Thr Phe Phe Asp Thr Pro Pro Met Leu
755                 760                 765                 770 ttt gtg ttc att gcc ctg ggc cgg tgg ctg gaa cac ttg gca aag agc   2830
Phe Val Phe Ile Ala Leu Gly Arg Trp Leu Glu His Leu Ala Lys Ser
            775                 780                 785 aaa acc tca gaa gcc ctg gct aaa ctc atg tct ctc caa gcc aca gaa   2878
Lys Thr Ser Glu Ala Leu Ala Lys Leu Met Ser Leu Gln Ala Thr Glu
        790                 795                 800 gcc acc gtt gtg acc ctt ggt gag gac aat tta atc atc agg gag gag   2926
Ala Thr Val Val Thr Leu Gly Glu Asp Asn Leu Ile Ile Arg Glu Glu
    805                 810                 815 caa gtc ccc atg gag ctg gtg cag cgg ggc gat atc gtc aag gtg gtc   2974
Gln Val Pro Met Glu Leu Val Gln Arg Gly Asp Ile Val Lys Val Val
820                 825                 830 cct ggg gga aag ttt cca gtg gat ggg aaa gtc ctg gaa ggc aat acc   3022
Pro Gly Gly Lys Phe Pro Val Asp Gly Lys Val Leu Glu Gly Asn Thr
835                 840                 845                 850 atg gct gat gag tcc ctc atc aca gga gaa gcc atg cca gtc act aag   3070
Met Ala Asp Glu Ser Leu Ile Thr Gly Glu Ala Met Pro Val Thr Lys
            855                 860                 865 aaa ccc gga agc act gta att gcg ggg tct ata aat gca cat ggc tct   3118
Lys Pro Gly Ser Thr Val Ile Ala Gly Ser Ile Asn Ala His Gly Ser
        870                 875                 880 gtg ctc att aaa gct acc cac gtg ggc aat gac acc act ttg gct cag   3166
Val Leu Ile Lys Ala Thr His Val Gly Asn Asp Thr Thr Leu Ala Gln
    885                 890                 895 att gtg aaa ctg gtg gaa gag gct cag atg tca aag gca ccc att cag   3214
Ile Val Lys Leu Val Glu Glu Ala Gln Met Ser Lys Ala Pro Ile Gln
900                 905                 910
```

| | |
|---|---|
| cag ctg gct gac cgg ttt agt gga tat ttt gtc cca ttt atc atc atc<br>Gln Leu Ala Asp Arg Phe Ser Gly Tyr Phe Val Pro Phe Ile Ile Ile<br>915                 920                 925                 930 | 3262 |
| atg tca act ttg acg ttg gtg gta tgg att gta atc ggt ttt atc gat<br>Met Ser Thr Leu Thr Leu Val Val Trp Ile Val Ile Gly Phe Ile Asp<br>        935                 940                 945 | 3310 |
| ttt ggt gtt gtt cag aga tac ttt cct aac ccc aac aag cac atc tcc<br>Phe Gly Val Val Gln Arg Tyr Phe Pro Asn Pro Asn Lys His Ile Ser<br>950                 955                 960 | 3358 |
| cag aca gag gtg atc atc cgg ttt gct ttc cag acg tcc atc acg gtg<br>Gln Thr Glu Val Ile Ile Arg Phe Ala Phe Gln Thr Ser Ile Thr Val<br>        965                 970                 975 | 3406 |
| ctg tgc att gcc tgc ccc tgc tcc ctg ggg ctg gcc acg ccc acg gct<br>Leu Cys Ile Ala Cys Pro Cys Ser Leu Gly Leu Ala Thr Pro Thr Ala<br>980                 985                 990 | 3454 |
| gtc atg gtg ggc acc ggg gtg gcc gcg cag aac ggc atc ctc atc aag<br>Val Met Val Gly Thr Gly Val Ala Ala Gln Asn Gly Ile Leu Ile Lys<br>995                 1000                1005                1010 | 3502 |
| gga ggc aag ccc ctg gag atg gcg cac aag ata aag act gtg atg ttt<br>Gly Gly Lys Pro Leu Glu Met Ala His Lys Ile Lys Thr Val Met Phe<br>                1015                1020                1025 | 3550 |
| gac aag act ggc acc att acc cat ggc gtc ccc agg gtc atg cgg gtg<br>Asp Lys Thr Gly Thr Ile Thr His Gly Val Pro Arg Val Met Arg Val<br>        1030                1035                1040 | 3598 |
| ctc ctg ctg ggg gat gtg gcc aca ctg ccc ctc agg aag gtt ctg gct<br>Leu Leu Leu Gly Asp Val Ala Thr Leu Pro Leu Arg Lys Val Leu Ala<br>                1045                1050                1055 | 3646 |
| gtg gtg ggg act gcg gag gcc agc agt gaa cac ccc ttg ggc gtg gca<br>Val Val Gly Thr Ala Glu Ala Ser Ser Glu His Pro Leu Gly Val Ala<br>        1060                1065                1070 | 3694 |
| gtc acc aaa tac tgt aaa gag gaa ctt gga aca gag acc ttg gga tac<br>Val Thr Lys Tyr Cys Lys Glu Glu Leu Gly Thr Glu Thr Leu Gly Tyr<br>1075                1080                1085                1090 | 3742 |
| tgc acg gac ttc cag gca gtg cca ggc tgt gga att ggg tgc aaa gtc<br>Cys Thr Asp Phe Gln Ala Val Pro Gly Cys Gly Ile Gly Cys Lys Val<br>                1095                1100                1105 | 3790 |
| agc aac gtg gaa ggc atc ctg gcc cac agt gag cgc cct ttg agt gca<br>Ser Asn Val Glu Gly Ile Leu Ala His Ser Glu Arg Pro Leu Ser Ala<br>        1110                1115                1120 | 3838 |
| ccg gcc agt cac ctg aat gag gct ggc agc ctt ccc gca gaa aaa gat<br>Pro Ala Ser His Leu Asn Glu Ala Gly Ser Leu Pro Ala Glu Lys Asp<br>                1125                1130                1135 | 3886 |
| gca gtc ccc cag acc ttc tct gtg ctg att gga aac cgt gag tgg ctg<br>Ala Val Pro Gln Thr Phe Ser Val Leu Ile Gly Asn Arg Glu Trp Leu<br>        1140                1145                1150 | 3934 |
| agg cgc aac ggt tta acc att tct agc gat gtc agt gac gct atg aca<br>Arg Arg Asn Gly Leu Thr Ile Ser Ser Asp Val Ser Asp Ala Met Thr<br>1155                1160                1165                1170 | 3982 |
| gac cac gag atg aaa gga cag aca gcc atc ctg gtg gct att gac ggt<br>Asp His Glu Met Lys Gly Gln Thr Ala Ile Leu Val Ala Ile Asp Gly<br>                1175                1180                1185 | 4030 |
| gtg ctc tgt ggg atg atc gca atc gca gac gct gtc aag cag gag gct<br>Val Leu Cys Gly Met Ile Ala Ile Ala Asp Ala Val Lys Gln Glu Ala<br>        1190                1195                1200 | 4078 |
| gcc ctg gct gtg cac acg ctg cag agc atg ggt gtg gac gtg gtt ctg<br>Ala Leu Ala Val His Thr Leu Gln Ser Met Gly Val Asp Val Val Leu<br>        1205                1210                1215 | 4126 |
| atc acg ggg gac aac cgg aag aca gcc aga gct att gcc acc cag gtt<br>Ile Thr Gly Asp Asn Arg Lys Thr Ala Arg Ala Ile Ala Thr Gln Val<br>1220                1225                1230 | 4174 |

```
ggc atc aac aaa gtc ttt gca gag gtg ctg cct tcg cac aag gtg gcc   4222
Gly Ile Asn Lys Val Phe Ala Glu Val Leu Pro Ser His Lys Val Ala
1235                1240                1245                1250 aag gtc cag gag ctc cag aat aaa ggg aag aaa gtc gcc atg gtg ggg   4270
Lys Val Gln Glu Leu Gln Asn Lys Gly Lys Lys Val Ala Met Val Gly
        1255                1260                1265 gat ggg gtc aat gac tcc ccg gcc ttg gcc cag gca gac atg ggt gtg   4318
Asp Gly Val Asn Asp Ser Pro Ala Leu Ala Gln Ala Asp Met Gly Val
    1270                1275                1280 gcc att ggc acc ggc acg gat gtg gcc atc gag gca gcc gac gtc gtc   4366
Ala Ile Gly Thr Gly Thr Asp Val Ala Ile Glu Ala Ala Asp Val Val
1285                1290                1295 ctt atc aga aat gat ttg ctg gat gtg gtg gct agc att cac ctt tcc   4414
Leu Ile Arg Asn Asp Leu Leu Asp Val Val Ala Ser Ile His Leu Ser
    1300                1305                1310 aag agg act gtc cga agg ata cgc atc aac ctg gtc ctg gca ctg att   4462
Lys Arg Thr Val Arg Arg Ile Arg Ile Asn Leu Val Leu Ala Leu Ile
1315                1320                1325                1330 tat aac ctg gtt ggg ata ccc att gca gca ggt gtc ttc atg ccc atc   4510
Tyr Asn Leu Val Gly Ile Pro Ile Ala Ala Gly Val Phe Met Pro Ile
                1335                1340                1345 ggc att gtg ctg cag ccc tgg atg ggc tca gcg gcc atg gca gcc tcc   4558
Gly Ile Val Leu Gln Pro Trp Met Gly Ser Ala Ala Met Ala Ala Ser
            1350                1355                1360 tct gtg tct gtg gtg ctc tca tcc ctg cag ctc aag tgc tat aag aag   4606
Ser Val Ser Val Val Leu Ser Ser Leu Gln Leu Lys Cys Tyr Lys Lys
        1365                1370                1375 cct gac ctg gag agg tat gag gca cag gcg cat ggc cac atg aag ccc   4654
Pro Asp Leu Glu Arg Tyr Glu Ala Gln Ala His Gly His Met Lys Pro
    1380                1385                1390 ctg acg gca tcc cag gtc agt gtg cac ata ggc atg gat gac agg tgg   4702
Leu Thr Ala Ser Gln Val Ser Val His Ile Gly Met Asp Asp Arg Trp
1395                1400                1405                1410 cgg gac tcc ccc agg gcc aca cca tgg gac cag gtc agc tat gtc agc   4750
Arg Asp Ser Pro Arg Ala Thr Pro Trp Asp Gln Val Ser Tyr Val Ser
                1415                1420                1425 cag gtg tcg ctg tcc tcc ctg acg tcc gac aag cca tct cgg cac agc   4798
Gln Val Ser Leu Ser Ser Leu Thr Ser Asp Lys Pro Ser Arg His Ser
            1430                1435                1440 gct gca gca gac gat gat ggg gac aag tgg tct ctg ctc ctg aat ggc   4846
Ala Ala Ala Asp Asp Asp Gly Asp Lys Trp Ser Leu Leu Leu Asn Gly
        1445                1450                1455 agg gat gag gag cag tac atc tga ggtaccaata aagacctctt attttcattc   4900
Arg Asp Glu Glu Gln Tyr Ile
    1460                1465 atcaggtgtg gttggttttt ttgtgtgggg gcggatccat cggatcccgt gcggaccgag   4960
cggccgcagg aacccctagt gatggagttg ccactccct ctctgcgcgc tcgctcgctc   5020
actgaggccg ggcgaccaaa ggtcgcccga cgcccgggct tgcccgggc ggcctcagtg   5080 agcgagcgag cgcgcagctg cctgcag                                      5107

<210> SEQ ID NO 2
<211> LENGTH: 5107
<212> TYPE: DNA
<213> ORGANISM: Artificial Sequence
<220> FEATURE:
<223> OTHER INFORMATION: Nucleic acid construct of expression vector
      AAV2-AAT-coATP7B
```

```
<220> FEATURE:
<221> NAME/KEY: repeat_region
<222> LOCATION: 1..141
<223> OTHER INFORMATION: /note="5' ITR of adeno-associated virus
      serotype 2"
<220> FEATURE:
<221> NAME/KEY: promoter
<222> LOCATION: 156..460
<223> OTHER INFORMATION: /note="alpha 1 antitrypsin"
<220> FEATURE:
<221> NAME/KEY: CDS
<222> LOCATION: 473..4870
<223> OTHER INFORMATION: /note="Codon optimized sequence encoding ATP7B"
      /transl_table=1
<220> FEATURE:
<221> NAME/KEY: polyA_signal
<222> LOCATION: 4877..4932
<220> FEATURE:
<221> NAME/KEY: repeat_region
<222> LOCATION: 4968..5107
<223> OTHER INFORMATION: /note="3' ITR of adeno-associated virus
      serotype 2"

<400> SEQUENCE: 2
```

| | | | | |
|---|---|---|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtcgcca cccccctccac cttggacaca | 180 |
| ggacgctgtg gtttctgagc caggtacaat gactcctttc ggtaagtgca gtggaagctg | 240 |
| tacactgccc aggcaaagcg tccgggcagc gtaggcgggc gactcagatc ccagccagtg | 300 |
| gacttagccc ctgtttgctc ctccgataac tggggtgacc ttggttaata ttcaccagca | 360 |
| gcctccccccg ttgcccctct ggatccactg cttaaatacg gacgaggaca gggccctgtc | 420 |
| tcctcagctt caggcaccac cactgacctg gacagtgaa gcggccgcca cc atg cca | 478 |
| | | | | | Met Pro |
| | | | | | 1 |

```
gaa cag gaa cgc cag atc aca gca aga gag gga gca agt cgg aaa atc      526
Glu Gln Glu Arg Gln Ile Thr Ala Arg Glu Gly Ala Ser Arg Lys Ile
        5                  10                  15 ctg agc aaa ctg agc ctg cca acc aga gca tgg gaa ccc gca atg aag      574
Leu Ser Lys Leu Ser Leu Pro Thr Arg Ala Trp Glu Pro Ala Met Lys
 20                  25                  30 aaa agc ttc gcc ttt gac aac gtg gga tac gag gga ggg ctg gat gga      622
Lys Ser Phe Ala Phe Asp Asn Val Gly Tyr Glu Gly Gly Leu Asp Gly
 35                  40                  45                  50 ctg gga cct agc tcc cag gtg gcc acc tct aca gtc cga atc ctg ggc      670
Leu Gly Pro Ser Ser Gln Val Ala Thr Ser Thr Val Arg Ile Leu Gly
                 55                  60                  65 atg act tgc cag agt tgc gtg aaa tca att gaa gac cgg atc agt aat      718
Met Thr Cys Gln Ser Cys Val Lys Ser Ile Glu Asp Arg Ile Ser Asn
         70                  75                  80 ctg aag gga atc att agc atg aaa gtg tcc ctg gag cag ggc tca gcc      766
Leu Lys Gly Ile Ile Ser Met Lys Val Ser Leu Glu Gln Gly Ser Ala
     85                  90                  95 acc gtg aag tat gtc cct agc gtg gtc tgc ctg cag cag gtg tgc cac      814
Thr Val Lys Tyr Val Pro Ser Val Val Cys Leu Gln Gln Val Cys His
100                 105                 110 cag atc ggc gat atg ggg ttc gag gcc tcc att gct gaa ggg aaa gcc      862
Gln Ile Gly Asp Met Gly Phe Glu Ala Ser Ile Ala Glu Gly Lys Ala
115                 120                 125                 130 gct tct tgg cct agc cgg tcc ctg cca gca cag gaa gca gtg gtc aag      910
Ala Ser Trp Pro Ser Arg Ser Leu Pro Ala Gln Glu Ala Val Val Lys
                135                 140                 145
```

```
ctg aga gtg gag gga atg aca tgc cag agc tgc gtg agc agt atc gaa    958
Leu Arg Val Glu Gly Met Thr Cys Gln Ser Cys Val Ser Ser Ile Glu
        150                 155                 160 gga aag gtc cga aaa ctg cag ggc gtg gtc cgg gtg aag gtc tct ctg   1006
Gly Lys Val Arg Lys Leu Gln Gly Val Val Arg Val Lys Val Ser Leu
    165                 170                 175 agt aac cag gag gcc gtg att acc tac cag ccc tat ctg atc cag cct   1054
Ser Asn Gln Glu Ala Val Ile Thr Tyr Gln Pro Tyr Leu Ile Gln Pro
180                 185                 190 gaa gac ctg agg gat cac gtg aat gac atg ggc ttc gag gca gcc atc   1102
Glu Asp Leu Arg Asp His Val Asn Asp Met Gly Phe Glu Ala Ala Ile
195                 200                 205                 210 aag tcc aaa gtg gcc cca ctg tct ctg ggg ccc att gat atc gaa aga   1150
Lys Ser Lys Val Ala Pro Leu Ser Leu Gly Pro Ile Asp Ile Glu Arg
        215                 220                 225 ctg cag tcc acc aac cca aag agg ccc ctg tca agc gcc aac cag aac   1198
Leu Gln Ser Thr Asn Pro Lys Arg Pro Leu Ser Ser Ala Asn Gln Asn
        230                 235                 240 ttc aac aat agt gag acc ctg gga cac cag ggc tca cat gtg gtc aca   1246
Phe Asn Asn Ser Glu Thr Leu Gly His Gln Gly Ser His Val Val Thr
    245                 250                 255 ctg cag ctg agg att gac ggc atg cac tgc aag tct tgc gtg ctg aac   1294
Leu Gln Leu Arg Ile Asp Gly Met His Cys Lys Ser Cys Val Leu Asn
260                 265                 270 att gag gaa aat atc ggc cag ctg ctg ggg gtg cag tct atc cag gtc   1342
Ile Glu Glu Asn Ile Gly Gln Leu Leu Gly Val Gln Ser Ile Gln Val
275                 280                 285                 290 agt ctg gag aac aag act gct cag gtg aaa tac gat cct tca tgc acc   1390
Ser Leu Glu Asn Lys Thr Ala Gln Val Lys Tyr Asp Pro Ser Cys Thr
        295                 300                 305 agc cca gtg gca ctg cag cgc gct atc gaa gca ctg ccc cct gga aat   1438
Ser Pro Val Ala Leu Gln Arg Ala Ile Glu Ala Leu Pro Pro Gly Asn
        310                 315                 320 ttc aag gtg agc ctg cct gac gga gca gag gga tcc gga acc gat cac   1486
Phe Lys Val Ser Leu Pro Asp Gly Ala Glu Gly Ser Gly Thr Asp His
    325                 330                 335 agg tcc tct agt tca cat tcc cca ggg tct cca cca cga aac cag gtg   1534
Arg Ser Ser Ser Ser His Ser Pro Gly Ser Pro Pro Arg Asn Gln Val
340                 345                 350 cag gga aca tgt tcc acc aca ctg att gca atc gcc ggc atg act tgc   1582
Gln Gly Thr Cys Ser Thr Thr Leu Ile Ala Ile Ala Gly Met Thr Cys
355                 360                 365                 370 gcc tca tgc gtg cac agc att gaa ggg atg atc tct cag ctg gag gga   1630
Ala Ser Cys Val His Ser Ile Glu Gly Met Ile Ser Gln Leu Glu Gly
        375                 380                 385 gtg cag cag atc tca gtc agc ctg gcc gag ggc act gct acc gtg ctg   1678
Val Gln Gln Ile Ser Val Ser Leu Ala Glu Gly Thr Ala Thr Val Leu
        390                 395                 400 tac aat ccc agt gtc atc tca cct gag gaa ctg cgg gct gca att gag   1726
Tyr Asn Pro Ser Val Ile Ser Pro Glu Glu Leu Arg Ala Ala Ile Glu
    405                 410                 415 gac atg ggg ttc gaa gct tcc gtg gtc tcc gaa tct tgc agt acc aac   1774
Asp Met Gly Phe Glu Ala Ser Val Val Ser Glu Ser Cys Ser Thr Asn
420                 425                 430 ccc ctg ggg aat cat tcc gcc gga aac tct atg gtg cag act acc gac   1822
Pro Leu Gly Asn His Ser Ala Gly Asn Ser Met Val Gln Thr Thr Asp
435                 440                 445                 450 ggg aca cct act tct gtg cag gag gtc gca cca cac aca gga cgc ctg   1870
Gly Thr Pro Thr Ser Val Gln Glu Val Ala Pro His Thr Gly Arg Leu
        455                 460                 465
```

-continued

| | | |
|---|---|---|
| cca gcc aat cat gct ccc gat atc ctg gcc aaa agc ccc cag tcc act<br>Pro Ala Asn His Ala Pro Asp Ile Leu Ala Lys Ser Pro Gln Ser Thr<br>          470                    475                    480 | 1918 |
| cga gct gtg gca cct cag aag tgt ttt ctg cag atc aaa ggc atg acc<br>Arg Ala Val Ala Pro Gln Lys Cys Phe Leu Gln Ile Lys Gly Met Thr<br>          485                    490                    495 | 1966 |
| tgc gcc tct tgc gtg agc aac att gag cgg aat ctg cag aag gaa gct<br>Cys Ala Ser Cys Val Ser Asn Ile Glu Arg Asn Leu Gln Lys Glu Ala<br>500                    505                    510 | 2014 |
| ggg gtg ctg agc gtg ctg gtc gca ctg atg gcc gga aag gct gag atc<br>Gly Val Leu Ser Val Leu Val Ala Leu Met Ala Gly Lys Ala Glu Ile<br>515                    520                    525                    530 | 2062 |
| aag tac gac cct gaa gtg atc cag cca ctg gag att gcc cag ttc atc<br>Lys Tyr Asp Pro Glu Val Ile Gln Pro Leu Glu Ile Ala Gln Phe Ile<br>                    535                    540                    545 | 2110 |
| cag gat ctg ggc ttt gag gcc gct gtg atg gaa gac tat gct ggg agc<br>Gln Asp Leu Gly Phe Glu Ala Ala Val Met Glu Asp Tyr Ala Gly Ser<br>          550                    555                    560 | 2158 |
| gat gga aac att gaa ctg acc atc acc gga atg act tgt gcc tct tgc<br>Asp Gly Asn Ile Glu Leu Thr Ile Thr Gly Met Thr Cys Ala Ser Cys<br>565                    570                    575 | 2206 |
| gtg cac aac atc gag agt aaa ctg act aga acc aat ggg att acc tac<br>Val His Asn Ile Glu Ser Lys Leu Thr Arg Thr Asn Gly Ile Thr Tyr<br>          580                    585                    590 | 2254 |
| gcc agt gtg gcc ctg gct aca tca aag gct ctg gtg aaa ttc gac ccc<br>Ala Ser Val Ala Leu Ala Thr Ser Lys Ala Leu Val Lys Phe Asp Pro<br>595                    600                    605                    610 | 2302 |
| gag atc att gga cct agg gat atc att aag atc att gag gaa atc ggc<br>Glu Ile Ile Gly Pro Arg Asp Ile Ile Lys Ile Ile Glu Glu Ile Gly<br>                    615                    620                    625 | 2350 |
| ttt cac gca agc ctg gcc cag cgc aac cca aat gcc cac cat ctg gac<br>Phe His Ala Ser Leu Ala Gln Arg Asn Pro Asn Ala His His Leu Asp<br>          630                    635                    640 | 2398 |
| cat aag atg gag atc aag cag tgg aag aaa agt ttc ctg tgc tca ctg<br>His Lys Met Glu Ile Lys Gln Trp Lys Lys Ser Phe Leu Cys Ser Leu<br>645                    650                    655 | 2446 |
| gtg ttt gga atc ccc gtc atg gcc ctg atg atc tac atg ctg atc cct<br>Val Phe Gly Ile Pro Val Met Ala Leu Met Ile Tyr Met Leu Ile Pro<br>          660                    665                    670 | 2494 |
| agc aac gag cca cac cag tcc atg gtg ctg gat cat aac atc att cct<br>Ser Asn Glu Pro His Gln Ser Met Val Leu Asp His Asn Ile Ile Pro<br>675                    680                    685                    690 | 2542 |
| ggc ctg tcc atc ctg aat ctg att ttc ttt atc ctg tgc aca ttc gtg<br>Gly Leu Ser Ile Leu Asn Leu Ile Phe Phe Ile Leu Cys Thr Phe Val<br>                    695                    700                    705 | 2590 |
| cag ctg ctg gga ggc tgg tac ttt tat gtg cag gca tat aaa tca ctg<br>Gln Leu Leu Gly Gly Trp Tyr Phe Tyr Val Gln Ala Tyr Lys Ser Leu<br>          710                    715                    720 | 2638 |
| cga cac cgg agc gcc aat atg gac gtg ctg att gtc ctg gca acc tct<br>Arg His Arg Ser Ala Asn Met Asp Val Leu Ile Val Leu Ala Thr Ser<br>725                    730                    735 | 2686 |
| atc gcc tac gtg tat agt ctg gtc atc ctg gtg gtc gca gtg gca gag<br>Ile Ala Tyr Val Tyr Ser Leu Val Ile Leu Val Val Ala Val Ala Glu<br>          740                    745                    750 | 2734 |
| aag gca gaa cgg agc cca gtg act ttc ttt gat acc cct cca atg ctg<br>Lys Ala Glu Arg Ser Pro Val Thr Phe Phe Asp Thr Pro Pro Met Leu<br>755                    760                    765                    770 | 2782 |
| ttc gtg ttt atc gct ctg ggc aga tgg ctg gaa cat ctg gca aag tca<br>Phe Val Phe Ile Ala Leu Gly Arg Trp Leu Glu His Leu Ala Lys Ser<br>                    775                    780                    785 | 2830 |

-continued

| | |
|---|---|
| aaa acc agc gag gct ctg gca aag ctg atg agc ctg cag gct acc gaa<br>Lys Thr Ser Glu Ala Leu Ala Lys Leu Met Ser Leu Gln Ala Thr Glu<br>          790                795                  800 | 2878 |
| gca aca gtg gtc act ctg gga gag gac aac ctg atc att cgc gag gaa<br>Ala Thr Val Val Thr Leu Gly Glu Asp Asn Leu Ile Ile Arg Glu Glu<br>          805                810                  815 | 2926 |
| cag gtg cct atg gaa ctg gtc cag cga ggc gat atc gtg aag gtg gtc<br>Gln Val Pro Met Glu Leu Val Gln Arg Gly Asp Ile Val Lys Val Val<br>820                  825                  830 | 2974 |
| cca ggg gga aaa ttc ccc gtg gac ggc aag gtc ctg gag ggg aat act<br>Pro Gly Gly Lys Phe Pro Val Asp Gly Lys Val Leu Glu Gly Asn Thr<br>835                  840                  845                  850 | 3022 |
| atg gcc gat gaa tcc ctg atc acc ggc gag gct atg cct gtg aca aag<br>Met Ala Asp Glu Ser Leu Ile Thr Gly Glu Ala Met Pro Val Thr Lys<br>                  855                  860                  865 | 3070 |
| aaa cca gga tca act gtc att gct ggc agc atc aac gca cac ggg tcc<br>Lys Pro Gly Ser Thr Val Ile Ala Gly Ser Ile Asn Ala His Gly Ser<br>          870                875                  880 | 3118 |
| gtg ctg atc aag gcc aca cat gtc ggg aat gac aca act ctg gct cag<br>Val Leu Ile Lys Ala Thr His Val Gly Asn Asp Thr Thr Leu Ala Gln<br>                  885                  890                  895 | 3166 |
| att gtg aaa ctg gtc gag gaa gcc cag atg tcc aag gct cct atc cag<br>Ile Val Lys Leu Val Glu Glu Ala Gln Met Ser Lys Ala Pro Ile Gln<br>900                  905                  910 | 3214 |
| cag ctg gcc gat cgg ttc tcc ggc tac ttc gtg ccc ttc atc att atc<br>Gln Leu Ala Asp Arg Phe Ser Gly Tyr Phe Val Pro Phe Ile Ile Ile<br>915                  920                  925                  930 | 3262 |
| atg tct aca ctg act ctg gtg gtc tgg att gtg atc gga ttc att gac<br>Met Ser Thr Leu Thr Leu Val Val Trp Ile Val Ile Gly Phe Ile Asp<br>                  935                  940                  945 | 3310 |
| ttt ggc gtg gtc cag aga tat ttt ccc aac cct aat aag cac atc agc<br>Phe Gly Val Val Gln Arg Tyr Phe Pro Asn Pro Asn Lys His Ile Ser<br>          950                955                  960 | 3358 |
| cag acc gaa gtg atc atc agg ttc gca ttt cag acc agt att aca gtg<br>Gln Thr Glu Val Ile Ile Arg Phe Ala Phe Gln Thr Ser Ile Thr Val<br>                  965                  970                  975 | 3406 |
| ctg tgc atc gcc tgc cca tgt tca ctg ggg ctg gct acc ccc aca gca<br>Leu Cys Ile Ala Cys Pro Cys Ser Leu Gly Leu Ala Thr Pro Thr Ala<br>980                  985                  990 | 3454 |
| gtg atg gtc gga aca gga gtg gca gca cag aac gga att ctg atc aag<br>Val Met Val Gly Thr Gly Val Ala Ala Gln Asn Gly Ile Leu Ile Lys<br>995                  1000                1005              1010 | 3502 |
| ggc ggg aaa ccc ctg gag atg gcc cac aag atc aaa act gtg atg ttt<br>Gly Gly Lys Pro Leu Glu Met Ala His Lys Ile Lys Thr Val Met Phe<br>                  1015                1020              1025 | 3550 |
| gac aaa act ggg acc att aca cat gga gtg ccc cgc gtc atg cga gtg<br>Asp Lys Thr Gly Thr Ile Thr His Gly Val Pro Arg Val Met Arg Val<br>          1030                1035              1040 | 3598 |
| ctg ctg ctg ggc gat gtg gca acc ctg cct ctg aga aag gtc ctg gca<br>Leu Leu Leu Gly Asp Val Ala Thr Leu Pro Leu Arg Lys Val Leu Ala<br>                  1045                1050              1055 | 3646 |
| gtg gtc gga aca gca gag gct agc tcc gaa cac cca ctg ggg gtg gcc<br>Val Val Gly Thr Ala Glu Ala Ser Ser Glu His Pro Leu Gly Val Ala<br>          1060                1065              1070 | 3694 |
| gtc aca aag tac tgc aaa gag gaa ctg ggc act gag acc ctg ggg tat<br>Val Thr Lys Tyr Cys Lys Glu Glu Leu Gly Thr Glu Thr Leu Gly Tyr<br>1075                1080                1085              1090 | 3742 |
| tgt act gac ttc cag gca gtg ccc gga tgc gga atc gga tgt aaa gtc<br>Cys Thr Asp Phe Gln Ala Val Pro Gly Cys Gly Ile Gly Cys Lys Val<br>                  1095                1100              1105 | 3790 |

```
                                    -continued tct aac gtg gaa ggg att ctg gct cac agt gag cgg ccc ctg agc gca    3838
Ser Asn Val Glu Gly Ile Leu Ala His Ser Glu Arg Pro Leu Ser Ala
        1110                1115                1120 cct gca tcc cat ctg aat gaa gca gga agc ctg cca gca gag aag gac    3886
Pro Ala Ser His Leu Asn Glu Ala Gly Ser Leu Pro Ala Glu Lys Asp
            1125                1130                1135 gct gtg cct cag acc ttt tcc gtc ctg atc ggc aac aga gaa tgg ctg    3934
Ala Val Pro Gln Thr Phe Ser Val Leu Ile Gly Asn Arg Glu Trp Leu
        1140                1145                1150 cgg aga aat ggg ctg aca att tct agt gac gtg tcc gat gcc atg aca    3982
Arg Arg Asn Gly Leu Thr Ile Ser Ser Asp Val Ser Asp Ala Met Thr
1155                1160                1165                1170 gat cac gag atg aaa ggc cag act gca att ctg gtg gcc atc gac gga    4030
Asp His Glu Met Lys Gly Gln Thr Ala Ile Leu Val Ala Ile Asp Gly
            1175                1180                1185 gtc ctg tgc ggc atg att gct atc gca gat gcc gtg aag cag gag gct    4078
Val Leu Cys Gly Met Ile Ala Ile Ala Asp Ala Val Lys Gln Glu Ala
        1190                1195                1200 gca ctg gcc gtc cat acc ctg cag tct atg ggc gtg gac gtg gtc ctg    4126
Ala Leu Ala Val His Thr Leu Gln Ser Met Gly Val Asp Val Val Leu
1205                1210                1215 atc acc ggg gat aac cgg aaa aca gct aga gca att gcc act caa gtg    4174
Ile Thr Gly Asp Asn Arg Lys Thr Ala Arg Ala Ile Ala Thr Gln Val
        1220                1225                1230 ggc atc aat aag gtg ttc gct gaa gtc ctg cct agc cac aag gtc gca    4222
Gly Ile Asn Lys Val Phe Ala Glu Val Leu Pro Ser His Lys Val Ala
1235                1240                1245                1250 aaa gtg cag gag ctg cag aac aag ggc aag aaa gtc gcc atg gtg gga    4270
Lys Val Gln Glu Leu Gln Asn Lys Gly Lys Lys Val Ala Met Val Gly
            1255                1260                1265 gac ggc gtg aat gat agc cca gct ctg gca cag gca gac atg gga gtc    4318
Asp Gly Val Asn Asp Ser Pro Ala Leu Ala Gln Ala Asp Met Gly Val
        1270                1275                1280 gct att ggg aca gga act gac gtg gca atc gag gcc gct gat gtg gtc    4366
Ala Ile Gly Thr Gly Thr Asp Val Ala Ile Glu Ala Ala Asp Val Val
    1285                1290                1295 ctg att agg aat gac ctg ctg gat gtg gtc gct tct att cat ctg agt    4414
Leu Ile Arg Asn Asp Leu Leu Asp Val Val Ala Ser Ile His Leu Ser
        1300                1305                1310 aag agg aca gtg agg cgc att cgc atc aac ctg gtg ctg gcc ctg atc    4462
Lys Arg Thr Val Arg Arg Ile Arg Ile Asn Leu Val Leu Ala Leu Ile
1315                1320                1325                1330 tac aat ctg gtg gga att cca atc gca gcc ggc gtg ttt atg cca att    4510
Tyr Asn Leu Val Gly Ile Pro Ile Ala Ala Gly Val Phe Met Pro Ile
            1335                1340                1345 ggg atc gtc ctg cag ccc tgg atg ggc tca gct gca atg gcc gct tca    4558
Gly Ile Val Leu Gln Pro Trp Met Gly Ser Ala Ala Met Ala Ala Ser
        1350                1355                1360 agc gtg agc gtg gtc ctg tcc tct ctg cag ctg aaa tgc tac aag aaa    4606
Ser Val Ser Val Val Leu Ser Ser Leu Gln Leu Lys Cys Tyr Lys Lys
            1365                1370                1375 cca gac ctg gag cgg tac gaa gct cag gca cac gga cat atg aag ccc    4654
Pro Asp Leu Glu Arg Tyr Glu Ala Gln Ala His Gly His Met Lys Pro
        1380                1385                1390 ctg acc gct tcc cag gtg tct gtc cac atc ggc atg gac gat aga tgg    4702
Leu Thr Ala Ser Gln Val Ser Val His Ile Gly Met Asp Asp Arg Trp
1395                1400                1405                1410 agg gac agc cca agg gcc act cca tgg gat cag gtc agt tac gtg agc    4750
Arg Asp Ser Pro Arg Ala Thr Pro Trp Asp Gln Val Ser Tyr Val Ser
            1415                1420                1425
```

-continued

```
cag gtc agc ctg agt tca ctg acc agc gac aag ccc tcc cgc cat tct      4798
Gln Val Ser Leu Ser Ser Leu Thr Ser Asp Lys Pro Ser Arg His Ser
        1430                1435                1440 gca gcc gct gat gac gac ggg gac aag tgg agc ctg ctg ctg aac gga      4846
Ala Ala Ala Asp Asp Asp Gly Asp Lys Trp Ser Leu Leu Leu Asn Gly
            1445                1450                1455 agg gac gaa gaa cag tat atc taa ggtaccaata aagacctctt attttcattc     4900
Arg Asp Glu Glu Gln Tyr Ile
        1460                1465 atcaggtgtg gttggttttt ttgtgtgggg gcggatccat cggatcccgt gcggaccgag    4960
cggccgcagg aaccccctagt gatggagttg gccactccct ctctgcgcgc tcgctcgctc   5020
actgaggccg ggcgaccaaa ggtcgcccga cgcccgggct tgcccgggc ggcctcagtg     5080 agcgagcgag cgcgcagctg cctgcag                                        5107
```

<210> SEQ ID NO 3
<211> LENGTH: 1465
<212> TYPE: PRT
<213> ORGANISM: Artificial Sequence
<220> FEATURE:
<223> OTHER INFORMATION: [CDS]:473..4870 from SEQ ID NO 1

<400> SEQUENCE: 3

```
Met Pro Glu Gln Glu Arg Gln Ile Thr Ala Arg Glu Gly Ala Ser Arg
1               5                   10                  15

Lys Ile Leu Ser Lys Leu Ser Leu Pro Thr Arg Ala Trp Glu Pro Ala
            20                  25                  30

Met Lys Lys Ser Phe Ala Phe Asp Asn Val Gly Tyr Glu Gly Gly Leu
        35                  40                  45

Asp Gly Leu Gly Pro Ser Ser Gln Val Ala Thr Ser Thr Val Arg Ile
    50                  55                  60

Leu Gly Met Thr Cys Gln Ser Cys Val Lys Ser Ile Glu Asp Arg Ile
65                  70                  75                  80

Ser Asn Leu Lys Gly Ile Ile Ser Met Lys Val Ser Leu Glu Gln Gly
                85                  90                  95

Ser Ala Thr Val Lys Tyr Val Pro Ser Val Val Cys Leu Gln Gln Val
            100                 105                 110

Cys His Gln Ile Gly Asp Met Gly Phe Glu Ala Ser Ile Ala Glu Gly
        115                 120                 125

Lys Ala Ala Ser Trp Pro Ser Arg Ser Leu Pro Ala Gln Glu Ala Val
    130                 135                 140

Val Lys Leu Arg Val Glu Gly Met Thr Cys Gln Ser Cys Val Ser Ser
145                 150                 155                 160

Ile Glu Gly Lys Val Arg Lys Leu Gln Gly Val Val Arg Val Lys Val
                165                 170                 175

Ser Leu Ser Asn Gln Glu Ala Val Ile Thr Tyr Gln Pro Tyr Leu Ile
            180                 185                 190

Gln Pro Glu Asp Leu Arg Asp His Val Asn Asp Met Gly Phe Glu Ala
        195                 200                 205

Ala Ile Lys Ser Lys Val Ala Pro Leu Ser Leu Gly Pro Ile Asp Ile
    210                 215                 220

Glu Arg Leu Gln Ser Thr Asn Pro Lys Arg Pro Leu Ser Ser Ala Asn
225                 230                 235                 240

Gln Asn Phe Asn Asn Ser Glu Thr Leu Gly His Gln Gly Ser His Val
                245                 250                 255
```

```
Val Thr Leu Gln Leu Arg Ile Asp Gly Met His Cys Lys Ser Cys Val
            260                 265                 270

Leu Asn Ile Glu Glu Asn Ile Gly Gln Leu Leu Gly Val Gln Ser Ile
        275                 280                 285

Gln Val Ser Leu Glu Asn Lys Thr Ala Gln Val Lys Tyr Asp Pro Ser
    290                 295                 300

Cys Thr Ser Pro Val Ala Leu Gln Arg Ala Ile Glu Ala Leu Pro Pro
305                 310                 315                 320

Gly Asn Phe Lys Val Ser Leu Pro Asp Gly Ala Glu Gly Ser Gly Thr
                325                 330                 335

Asp His Arg Ser Ser Ser Ser His Ser Pro Gly Ser Pro Pro Arg Asn
            340                 345                 350

Gln Val Gln Gly Thr Cys Ser Thr Thr Leu Ile Ala Ile Ala Gly Met
        355                 360                 365

Thr Cys Ala Ser Cys Val His Ser Ile Glu Gly Met Ile Ser Gln Leu
    370                 375                 380

Glu Gly Val Gln Gln Ile Ser Val Ser Leu Ala Glu Gly Thr Ala Thr
385                 390                 395                 400

Val Leu Tyr Asn Pro Ser Val Ile Ser Pro Glu Glu Leu Arg Ala Ala
                405                 410                 415

Ile Glu Asp Met Gly Phe Glu Ala Ser Val Val Ser Glu Ser Cys Ser
            420                 425                 430

Thr Asn Pro Leu Gly Asn His Ser Ala Gly Asn Ser Met Val Gln Thr
        435                 440                 445

Thr Asp Gly Thr Pro Thr Ser Val Gln Glu Val Ala Pro His Thr Gly
    450                 455                 460

Arg Leu Pro Ala Asn His Ala Pro Asp Ile Leu Ala Lys Ser Pro Gln
465                 470                 475                 480

Ser Thr Arg Ala Val Ala Pro Gln Lys Cys Phe Leu Gln Ile Lys Gly
                485                 490                 495

Met Thr Cys Ala Ser Cys Val Ser Asn Ile Glu Arg Asn Leu Gln Lys
            500                 505                 510

Glu Ala Gly Val Leu Ser Val Leu Val Ala Leu Met Ala Gly Lys Ala
        515                 520                 525

Glu Ile Lys Tyr Asp Pro Glu Val Ile Gln Pro Leu Glu Ile Ala Gln
    530                 535                 540

Phe Ile Gln Asp Leu Gly Phe Glu Ala Ala Val Met Glu Asp Tyr Ala
545                 550                 555                 560

Gly Ser Asp Gly Asn Ile Glu Leu Thr Ile Thr Gly Met Thr Cys Ala
                565                 570                 575

Ser Cys Val His Asn Ile Glu Ser Lys Leu Thr Arg Thr Asn Gly Ile
            580                 585                 590

Thr Tyr Ala Ser Val Ala Leu Ala Thr Ser Lys Ala Leu Val Lys Phe
        595                 600                 605

Asp Pro Glu Ile Ile Gly Pro Arg Asp Ile Ile Lys Ile Ile Glu Glu
    610                 615                 620

Ile Gly Phe His Ala Ser Leu Ala Gln Arg Asn Pro Asn Ala His His
625                 630                 635                 640

Leu Asp His Lys Met Glu Ile Lys Gln Trp Lys Lys Ser Phe Leu Cys
                645                 650                 655

Ser Leu Val Phe Gly Ile Pro Val Met Ala Leu Met Ile Tyr Met Leu
            660                 665                 670
```

```
Ile Pro Ser Asn Glu Pro His Gln Ser Met Val Leu Asp His Asn Ile
            675                 680                 685
Ile Pro Gly Leu Ser Ile Leu Asn Leu Ile Phe Phe Ile Leu Cys Thr
    690                 695                 700
Phe Val Gln Leu Leu Gly Gly Trp Tyr Phe Tyr Val Gln Ala Tyr Lys
705                 710                 715                 720
Ser Leu Arg His Arg Ser Ala Asn Met Asp Val Leu Ile Val Leu Ala
                725                 730                 735
Thr Ser Ile Ala Tyr Val Tyr Ser Leu Val Ile Leu Val Val Ala Val
            740                 745                 750
Ala Glu Lys Ala Glu Arg Ser Pro Val Thr Phe Phe Asp Thr Pro Pro
        755                 760                 765
Met Leu Phe Val Phe Ile Ala Leu Gly Arg Trp Leu Glu His Leu Ala
    770                 775                 780
Lys Ser Lys Thr Ser Glu Ala Leu Ala Lys Leu Met Ser Leu Gln Ala
785                 790                 795                 800
Thr Glu Ala Thr Val Val Thr Leu Gly Glu Asp Asn Leu Ile Ile Arg
                805                 810                 815
Glu Glu Gln Val Pro Met Glu Leu Val Gln Arg Gly Asp Ile Val Lys
            820                 825                 830
Val Val Pro Gly Gly Lys Phe Pro Val Asp Gly Lys Val Leu Glu Gly
        835                 840                 845
Asn Thr Met Ala Asp Glu Ser Leu Ile Thr Gly Glu Ala Met Pro Val
    850                 855                 860
Thr Lys Lys Pro Gly Ser Thr Val Ile Ala Gly Ser Ile Asn Ala His
865                 870                 875                 880
Gly Ser Val Leu Ile Lys Ala Thr His Val Gly Asn Asp Thr Thr Leu
                885                 890                 895
Ala Gln Ile Val Lys Leu Val Glu Glu Ala Gln Met Ser Lys Ala Pro
            900                 905                 910
Ile Gln Gln Leu Ala Asp Arg Phe Ser Gly Tyr Phe Val Pro Phe Ile
        915                 920                 925
Ile Ile Met Ser Thr Leu Thr Leu Val Val Trp Ile Val Ile Gly Phe
    930                 935                 940
Ile Asp Phe Gly Val Val Gln Arg Tyr Phe Pro Asn Pro Asn Lys His
945                 950                 955                 960
Ile Ser Gln Thr Glu Val Ile Ile Arg Phe Ala Phe Gln Thr Ser Ile
                965                 970                 975
Thr Val Leu Cys Ile Ala Cys Pro Cys Ser Leu Gly Leu Ala Thr Pro
            980                 985                 990
Thr Ala Val Met Val Gly Thr Gly Val Ala Ala Gln Asn Gly Ile Leu
        995                 1000                1005
Ile Lys Gly Gly Lys Pro Leu Glu Met Ala His Lys Ile Lys Thr Val
    1010                1015                1020
Met Phe Asp Lys Thr Gly Thr Ile Thr His Gly Val Pro Arg Val Met
1025                1030                1035                1040
Arg Val Leu Leu Leu Gly Asp Val Ala Thr Leu Pro Leu Arg Lys Val
                1045                1050                1055
Leu Ala Val Val Gly Thr Ala Glu Ala Ser Ser Glu His Pro Leu Gly
            1060                1065                1070
Val Ala Val Thr Lys Tyr Cys Lys Glu Glu Leu Gly Thr Glu Thr Leu
        1075                1080                1085
```

```
Gly Tyr Cys Thr Asp Phe Gln Ala Val Pro Gly Cys Gly Ile Gly Cys
    1090                1095                1100

Lys Val Ser Asn Val Glu Gly Ile Leu Ala His Ser Glu Arg Pro Leu
1105                1110                1115                1120

Ser Ala Pro Ala Ser His Leu Asn Glu Ala Gly Ser Leu Pro Ala Glu
            1125                1130                1135

Lys Asp Ala Val Pro Gln Thr Phe Ser Val Leu Ile Gly Asn Arg Glu
        1140                1145                1150

Trp Leu Arg Arg Asn Gly Leu Thr Ile Ser Ser Asp Val Ser Asp Ala
    1155                1160                1165

Met Thr Asp His Glu Met Lys Gly Gln Thr Ala Ile Leu Val Ala Ile
1170                1175                1180

Asp Gly Val Leu Cys Gly Met Ile Ala Ile Ala Asp Ala Val Lys Gln
1185                1190                1195                1200

Glu Ala Ala Leu Ala Val His Thr Leu Gln Ser Met Gly Val Asp Val
            1205                1210                1215

Val Leu Ile Thr Gly Asp Asn Arg Lys Thr Ala Arg Ala Ile Ala Thr
        1220                1225                1230

Gln Val Gly Ile Asn Lys Val Phe Ala Glu Val Leu Pro Ser His Lys
    1235                1240                1245

Val Ala Lys Val Gln Glu Leu Gln Asn Lys Gly Lys Lys Val Ala Met
1250                1255                1260

Val Gly Asp Gly Val Asn Asp Ser Pro Ala Leu Ala Gln Ala Asp Met
1265                1270                1275                1280

Gly Val Ala Ile Gly Thr Gly Thr Asp Val Ala Ile Glu Ala Ala Asp
            1285                1290                1295

Val Val Leu Ile Arg Asn Asp Leu Leu Asp Val Val Ala Ser Ile His
        1300                1305                1310

Leu Ser Lys Arg Thr Val Arg Arg Ile Arg Ile Asn Leu Val Leu Ala
    1315                1320                1325

Leu Ile Tyr Asn Leu Val Gly Ile Pro Ile Ala Ala Gly Val Phe Met
1330                1335                1340

Pro Ile Gly Ile Val Leu Gln Pro Trp Met Gly Ser Ala Ala Met Ala
1345                1350                1355                1360

Ala Ser Ser Val Ser Val Val Leu Ser Ser Leu Gln Leu Lys Cys Tyr
            1365                1370                1375

Lys Lys Pro Asp Leu Glu Arg Tyr Glu Ala Gln Ala His Gly His Met
        1380                1385                1390

Lys Pro Leu Thr Ala Ser Gln Val Ser Val His Ile Gly Met Asp Asp
    1395                1400                1405

Arg Trp Arg Asp Ser Pro Arg Ala Thr Pro Trp Asp Gln Val Ser Tyr
1410                1415                1420

Val Ser Gln Val Ser Leu Ser Ser Leu Thr Ser Asp Lys Pro Ser Arg
1425                1430                1435                1440

His Ser Ala Ala Ala Asp Asp Asp Gly Asp Lys Trp Ser Leu Leu Leu
            1445                1450                1455

Asn Gly Arg Asp Glu Glu Gln Tyr Ile
        1460                1465

<210> SEQ ID NO 4
<211> LENGTH: 1465
<212> TYPE: PRT
<213> ORGANISM: Artificial Sequence
<220> FEATURE:
<223> OTHER INFORMATION: [CDS]:473..4870 from SEQ ID NO 2
```

```
<400> SEQUENCE: 4

Met Pro Glu Gln Glu Arg Gln Ile Thr Ala Arg Glu Gly Ala Ser Arg
1               5                   10                  15

Lys Ile Leu Ser Lys Leu Ser Leu Pro Thr Arg Ala Trp Glu Pro Ala
                20                  25                  30

Met Lys Lys Ser Phe Ala Phe Asp Asn Val Gly Tyr Glu Gly Gly Leu
            35                  40                  45

Asp Gly Leu Gly Pro Ser Ser Gln Val Ala Thr Ser Thr Val Arg Ile
    50                  55                  60

Leu Gly Met Thr Cys Gln Ser Cys Val Lys Ser Ile Glu Asp Arg Ile
65                  70                  75                  80

Ser Asn Leu Lys Gly Ile Ile Ser Met Lys Val Ser Leu Glu Gln Gly
                85                  90                  95

Ser Ala Thr Val Lys Tyr Val Pro Ser Val Val Cys Leu Gln Gln Val
            100                 105                 110

Cys His Gln Ile Gly Asp Met Gly Phe Glu Ala Ser Ile Ala Glu Gly
        115                 120                 125

Lys Ala Ala Ser Trp Pro Ser Arg Ser Leu Pro Ala Gln Glu Ala Val
    130                 135                 140

Val Lys Leu Arg Val Glu Gly Met Thr Cys Gln Ser Cys Val Ser Ser
145                 150                 155                 160

Ile Glu Gly Lys Val Arg Lys Leu Gln Gly Val Val Arg Val Lys Val
                165                 170                 175

Ser Leu Ser Asn Gln Glu Ala Val Ile Thr Tyr Gln Pro Tyr Leu Ile
            180                 185                 190

Gln Pro Glu Asp Leu Arg Asp His Val Asn Asp Met Gly Phe Glu Ala
        195                 200                 205

Ala Ile Lys Ser Lys Val Ala Pro Leu Ser Leu Gly Pro Ile Asp Ile
    210                 215                 220

Glu Arg Leu Gln Ser Thr Asn Pro Lys Arg Pro Leu Ser Ser Ala Asn
225                 230                 235                 240

Gln Asn Phe Asn Asn Ser Glu Thr Leu Gly His Gln Gly Ser His Val
                245                 250                 255

Val Thr Leu Gln Leu Arg Ile Asp Gly Met His Cys Lys Ser Cys Val
            260                 265                 270

Leu Asn Ile Glu Glu Asn Ile Gly Gln Leu Leu Gly Val Gln Ser Ile
        275                 280                 285

Gln Val Ser Leu Glu Asn Lys Thr Ala Gln Val Lys Tyr Asp Pro Ser
    290                 295                 300

Cys Thr Ser Pro Val Ala Leu Gln Arg Ala Ile Glu Ala Leu Pro Pro
305                 310                 315                 320

Gly Asn Phe Lys Val Ser Leu Pro Asp Gly Ala Glu Gly Ser Gly Thr
                325                 330                 335

Asp His Arg Ser Ser Ser Ser His Ser Pro Gly Ser Pro Pro Arg Asn
            340                 345                 350

Gln Val Gln Gly Thr Cys Ser Thr Thr Leu Ile Ala Ile Ala Gly Met
        355                 360                 365

Thr Cys Ala Ser Cys Val His Ser Ile Glu Gly Met Ile Ser Gln Leu
    370                 375                 380

Glu Gly Val Gln Gln Ile Ser Val Ser Leu Ala Glu Gly Thr Ala Thr
385                 390                 395                 400

Val Leu Tyr Asn Pro Ser Val Ile Ser Pro Glu Glu Leu Arg Ala Ala
                405                 410                 415
```

```
Ile Glu Asp Met Gly Phe Glu Ala Ser Val Val Ser Glu Ser Cys Ser
                420                 425                 430

Thr Asn Pro Leu Gly Asn His Ser Ala Gly Asn Ser Met Val Gln Thr
            435                 440                 445

Thr Asp Gly Thr Pro Thr Ser Val Gln Glu Val Ala Pro His Thr Gly
        450                 455                 460

Arg Leu Pro Ala Asn His Ala Pro Asp Ile Leu Ala Lys Ser Pro Gln
465                 470                 475                 480

Ser Thr Arg Ala Val Ala Pro Gln Lys Cys Phe Leu Gln Ile Lys Gly
                485                 490                 495

Met Thr Cys Ala Ser Cys Val Ser Asn Ile Glu Arg Asn Leu Gln Lys
            500                 505                 510

Glu Ala Gly Val Leu Ser Val Leu Val Ala Leu Met Ala Gly Lys Ala
        515                 520                 525

Glu Ile Lys Tyr Asp Pro Glu Val Ile Gln Pro Leu Glu Ile Ala Gln
        530                 535                 540

Phe Ile Gln Asp Leu Gly Phe Glu Ala Ala Val Met Glu Asp Tyr Ala
545                 550                 555                 560

Gly Ser Asp Gly Asn Ile Glu Leu Thr Ile Thr Gly Met Thr Cys Ala
                565                 570                 575

Ser Cys Val His Asn Ile Glu Ser Lys Leu Thr Arg Thr Asn Gly Ile
            580                 585                 590

Thr Tyr Ala Ser Val Ala Leu Ala Thr Ser Lys Ala Leu Val Lys Phe
        595                 600                 605

Asp Pro Glu Ile Ile Gly Pro Arg Asp Ile Ile Lys Ile Ile Glu Glu
610                 615                 620

Ile Gly Phe His Ala Ser Leu Ala Gln Arg Asn Pro Asn Ala His His
625                 630                 635                 640

Leu Asp His Lys Met Glu Ile Lys Gln Trp Lys Lys Ser Phe Leu Cys
            645                 650                 655

Ser Leu Val Phe Gly Ile Pro Val Met Ala Leu Met Ile Tyr Met Leu
            660                 665                 670

Ile Pro Ser Asn Glu Pro His Gln Ser Met Val Leu Asp His Asn Ile
        675                 680                 685

Ile Pro Gly Leu Ser Ile Leu Asn Leu Ile Phe Phe Ile Leu Cys Thr
690                 695                 700

Phe Val Gln Leu Leu Gly Gly Trp Tyr Phe Tyr Val Gln Ala Tyr Lys
705                 710                 715                 720

Ser Leu Arg His Arg Ser Ala Asn Met Asp Val Leu Ile Val Leu Ala
                725                 730                 735

Thr Ser Ile Ala Tyr Val Tyr Ser Leu Val Ile Leu Val Val Ala Val
            740                 745                 750

Ala Glu Lys Ala Glu Arg Ser Pro Val Thr Phe Phe Asp Thr Pro Pro
        755                 760                 765

Met Leu Phe Val Phe Ile Ala Leu Gly Arg Trp Leu Glu His Leu Ala
770                 775                 780

Lys Ser Lys Thr Ser Glu Ala Leu Ala Lys Leu Met Ser Leu Gln Ala
785                 790                 795                 800

Thr Glu Ala Thr Val Val Thr Leu Gly Glu Asp Asn Leu Ile Ile Arg
                805                 810                 815

Glu Glu Gln Val Pro Met Glu Leu Val Gln Arg Gly Asp Ile Val Lys
            820                 825                 830
```

Val Val Pro Gly Gly Lys Phe Pro Val Asp Gly Lys Val Leu Glu Gly
            835                 840                 845

Asn Thr Met Ala Asp Glu Ser Leu Ile Thr Gly Glu Ala Met Pro Val
850                 855                 860

Thr Lys Lys Pro Gly Ser Thr Val Ile Ala Gly Ser Ile Asn Ala His
865                 870                 875                 880

Gly Ser Val Leu Ile Lys Ala Thr His Val Gly Asn Asp Thr Thr Leu
                885                 890                 895

Ala Gln Ile Val Lys Leu Val Glu Glu Ala Gln Met Ser Lys Ala Pro
                900                 905                 910

Ile Gln Gln Leu Ala Asp Arg Phe Ser Gly Tyr Phe Val Pro Phe Ile
                915                 920                 925

Ile Ile Met Ser Thr Leu Thr Leu Val Val Trp Ile Val Ile Gly Phe
                930                 935                 940

Ile Asp Phe Gly Val Val Gln Arg Tyr Phe Pro Asn Pro Asn Lys His
945                 950                 955                 960

Ile Ser Gln Thr Glu Val Ile Ile Arg Phe Ala Phe Gln Thr Ser Ile
                965                 970                 975

Thr Val Leu Cys Ile Ala Cys Pro Cys Ser Leu Gly Leu Ala Thr Pro
                980                 985                 990

Thr Ala Val Met Val Gly Thr Gly Val Ala Ala Gln Asn Gly Ile Leu
                995                 1000                1005

Ile Lys Gly Gly Lys Pro Leu Glu Met Ala His Lys Ile Lys Thr Val
                1010                1015                1020

Met Phe Asp Lys Thr Gly Thr Ile Thr His Gly Val Pro Arg Val Met
1025                1030                1035                1040

Arg Val Leu Leu Leu Gly Asp Val Ala Thr Leu Pro Leu Arg Lys Val
                1045                1050                1055

Leu Ala Val Val Gly Thr Ala Glu Ala Ser Ser Glu His Pro Leu Gly
                1060                1065                1070

Val Ala Val Thr Lys Tyr Cys Lys Glu Glu Leu Gly Thr Glu Thr Leu
                1075                1080                1085

Gly Tyr Cys Thr Asp Phe Gln Ala Val Pro Gly Cys Gly Ile Gly Cys
                1090                1095                1100

Lys Val Ser Asn Val Glu Gly Ile Leu Ala His Ser Glu Arg Pro Leu
1105                1110                1115                1120

Ser Ala Pro Ala Ser His Leu Asn Glu Ala Gly Ser Leu Pro Ala Glu
                1125                1130                1135

Lys Asp Ala Val Pro Gln Thr Phe Ser Val Leu Ile Gly Asn Arg Glu
                1140                1145                1150

Trp Leu Arg Arg Asn Gly Leu Thr Ile Ser Ser Asp Val Ser Asp Ala
                1155                1160                1165

Met Thr Asp His Glu Met Lys Gly Gln Thr Ala Ile Leu Val Ala Ile
                1170                1175                1180

Asp Gly Val Leu Cys Gly Met Ile Ala Ile Ala Asp Ala Val Lys Gln
1185                1190                1195                1200

Glu Ala Ala Leu Ala Val His Thr Leu Gln Ser Met Gly Val Asp Val
                1205                1210                1215

Val Leu Ile Thr Gly Asp Asn Arg Lys Thr Ala Arg Ala Ile Ala Thr
                1220                1225                1230

Gln Val Gly Ile Asn Lys Val Phe Ala Glu Val Leu Pro Ser His Lys
                1235                1240                1245

```
Val Ala Lys Val Gln Glu Leu Gln Asn Lys Gly Lys Lys Val Ala Met
     1250                1255                1260

Val Gly Asp Gly Val Asn Asp Ser Pro Ala Leu Ala Gln Ala Asp Met
1265                1270                1275                1280

Gly Val Ala Ile Gly Thr Gly Thr Asp Val Ala Ile Glu Ala Ala Asp
                1285                1290                1295

Val Val Leu Ile Arg Asn Asp Leu Leu Asp Val Val Ala Ser Ile His
            1300                1305                1310

Leu Ser Lys Arg Thr Val Arg Arg Ile Arg Ile Asn Leu Val Leu Ala
                1315                1320                1325

Leu Ile Tyr Asn Leu Val Gly Ile Pro Ile Ala Ala Gly Val Phe Met
        1330                1335                1340

Pro Ile Gly Ile Val Leu Gln Pro Trp Met Gly Ser Ala Ala Met Ala
1345                1350                1355                1360

Ala Ser Ser Val Ser Val Val Leu Ser Ser Leu Gln Leu Lys Cys Tyr
                1365                1370                1375

Lys Lys Pro Asp Leu Glu Arg Tyr Glu Ala Gln Ala His Gly His Met
            1380                1385                1390

Lys Pro Leu Thr Ala Ser Gln Val Ser Val His Ile Gly Met Asp Asp
        1395                1400                1405

Arg Trp Arg Asp Ser Pro Arg Ala Thr Pro Trp Asp Gln Val Ser Tyr
    1410                1415                1420

Val Ser Gln Val Ser Leu Ser Ser Leu Thr Ser Asp Lys Pro Ser Arg
1425                1430                1435                1440

His Ser Ala Ala Ala Asp Asp Asp Gly Asp Lys Trp Ser Leu Leu Leu
                1445                1450                1455

Asn Gly Arg Asp Glu Glu Gln Tyr Ile
            1460                1465

<210> SEQ ID NO 5
<211> LENGTH: 36
<212> TYPE: DNA
<213> ORGANISM: Artificial Sequence
<220> FEATURE:
<223> OTHER INFORMATION: Primer AAT-Forward

<400> SEQUENCE: 5
ctggtctaga acgcgtcgcc accccctcca ccttgg                              36

<210> SEQ ID NO 6
<211> LENGTH: 36
<212> TYPE: DNA
<213> ORGANISM: Artificial Sequence
<220> FEATURE:
<223> OTHER INFORMATION: Primer AAT-Reverse

<400> SEQUENCE: 6
atcatgatgc ggccgcttca ctgtcccagg tcagtg                              36
```

NUCLEIC ACID CONSTRUCTS AND GENE THERAPY VECTORS FOR USE IN THE TREATMENT OF WILSON'S DISEASE AND OTHER CONDITIONS

FIELD OF THE INVENTION

The present invention relates to nucleic acid constructs and gene therapy vectors for use in the treatment of Wilson's disease and other conditions.

BACKGROUND ART

The state of the art regarding gene therapy of Wilson's disease was reviewed by Merle et al. (*Current Gene Therapy* 2007; 7: 217-220) and is here summarized and completed with later disclosed references.

Wilson's disease (WD) is an autosomal recessively inherited disorder of copper metabolism with an average prevalence of 1:30,000. WD is caused by mutations of the ATP7B gene coding for a P-type copper transporting ATPase, which is located on chromosome 13. ATP7B is expressed mainly in hepatocytes and functions in the transmembrane transport of copper. Absent or reduced function of ATP7B protein leads to decreased hepatocellular excretion of copper into bile and results in copper accumulation primarily in the liver and subsequently in the neurologic system and other tissues. Failure to incorporate copper into ceruloplasmin is an additional consequence of the loss of functional ATP7B protein.

WD can present clinically as liver disease, as a progressive neurologic disorder, or as psychiatric illness. Patients with hepatic WD usually present in late childhood or adolescence, and exhibit features of acute hepatitis, fulminant hepatic failure, or progressive chronic liver disease. Neurologic manifestations of WD typically present later than the liver disease, most often in the second or third decade and include extrapyramidal, cerebellar and cerebral-related symptoms.

The aim of medical treatment of WD is to remove the toxic deposit of copper from the body and to prevent its reaccumulation. Three anti-copper drugs are currently approved for WD: D-penicillamine, trientine, and zinc salts. Medical therapy is effective in most, but not all patients with WD. Liver transplantation is a therapeutic option in WD patients presenting with fulminant liver failure or progressive liver failure. It has been shown to correct the WD phenotype and provides excellent long-term survival.

However, an interruption of therapy or inadequate treatment can lead to fatalities within few months. Because WD medication has to be taken regularly, adherence to treatment in some patients, especially in adolescent WD patients, is poor.

Under therapy residual neurological symptoms are relatively common and even progressive symptoms can occur. Because current medical treatment options are not in all WD patients effective and adherence to therapy is a problem, a more comprehensive solution could involve gene therapy.

Theoretically, expression of wild type ATP7B in hepatocytes would reverse all disease-related abnormalities and rescue the liver and the neurological symptoms. The ultimate goal of an ideal gene therapy for WD would be to deliver ATP7B, in sufficient quantity, specifically to hepatocytes for a lifelong duration.

All published studies on adenoviral gene transfer for WD have used early-generation adenoviral vectors producing only transient transgene expression. Terada et al. [Terada et al. *J. Biol. Chem.* 1998; 273:1815-1820; Terada et al. *FEBS Lett.* 1999; 448: 53-56] demonstrated successful gene transfer by adenovirus mediated gene delivery in the LEC rat model. Restoration of holoceruloplasmin synthesis, of serum ceruloplasmin oxidase activity, and of copper excretion in bile was shown, indicating a therapeutic effect of the gene transfer. These effects were of a very limited duration, with a maximum level at day three and a decline thereafter. Ha-Hao et al. [*Z. Gastroenterol.* 2002; 40: 209-216] also demonstrated an increased copper content in stool of LEC rats after adenovirus-mediated ATP7B gene transfer, indicating increased copper excretion into the bile. The therapeutic effect was in addition demonstrated by restoration of holoceruloplasmin and of its ferroxidase activity. However, once again the duration of the therapeutic effect in these experiments was only transient with a limited duration of a few days.

Gutless adenoviral vectors have not been tested for this application so far.

Other commonly used non-integrating viral vector system, the adeno-associated virus (AAV), has neither been tested for WD so far, mainly because the ATP7B gene (approximately 4.4 kb large) leaves minimum space for allocating the rest of required sequences (e.g. promoter, poly A signal sequence, etc) within the AAV vector, whose packaging capacity is 4.4-4.7 kb. German patent application DE 100156121A1 (published 2003) proposed a recombinant adeno-associated viral vector for the gene therapy of WD that possesses a shortened metal-sensitive promoter (metallothionein-I promoter) to produce copper or zinc inducible expression of ATP7B transgene. Nevertheless, this document does not provide, nor has been later disclosed, any information regarding the therapeutic efficiency and performance of the vector.

On the other hand, several lentiviral vectors carrying wild type ATP7B have been tested in animal models of WD. Merle et al. [*Scan. J. Gastroenterol.* 2006; 41: 974-982] reported systemic gene therapy in LEC rats with lentiviral vectors expressing ATP7B under the control of a phosphoglycerokinase promoter. Twenty-four weeks after gene transfer liver copper content was lowered significantly and liver histology improved in treated rats compared to untreated controls, but the effect was only partial. Serum ceruloplasmin oxidase activity was increased two weeks after gene transfer when compared to controls, however, it declined to lower levels 24 weeks after treatment. More recently, Roybal et al. [*Gene Therapy* 2012; 19: 1085-1094] have reported early gestational gene transfer in ATP7B$^{-/-}$ mice with a lentivirus carrying human ATP7B under transcriptional control of a liver-specific promoter which contained element of apolipoprotein E and alpha-1 antitrypsin. In utero administration of the vector provided a decrease in liver copper levels, preservation of normal hepatic histology, restoration of copper incorporation into ceruloplasmin and improved cholesterol biosynthesis. However, the efficiency of the treatment was very variable from mice to mice and declined with time.

SUMMARY OF THE INVENTION

The inventors have for the first time engineered an adeno-associated viral vector which administered to ATP7B knockout mice (a recognized animal model of Wilson's disease) corrected main Wilson's disease pathological features for at least 24 weeks after treatment. This AAV vector, herein referred to as AAV2/8-AAT-wtATP7B, carries a gene encoding human ATP7B under transcriptional control of a liver-specific promoter which merely contains the core promoter sequence of α1-antitrypsin gene (AAT). Cu excretion (Cu urine content), and liver Cu content were significantly reduced in Wilson's disease mice treated with the vector, while ceruloplasmin activity was significantly restored. Furthermore, said AAV vector restored physiological biliary copper excretion. On the other hand, the administration of the vector resulted in the normalization of serum transaminases levels and of liver histology, together with a marked reduction of the inflammatory infiltrate, biliary duct proliferation and fibrosis. These observations indicated that both the nucleic acid construct (AAT promoter linked to sequence encoding ATP7B) and the 5.1 kb long AAV vector which carries it enable to overcome the most relevant pathological effects of an accumulation of copper linked to a deficiency or dysfunction of ATP7B and thus can be very suitable for gene therapy in the treatment of a condition caused by a deficiency or dysfunction of Copper-transporting ATPase 2, such as Wilson's disease or a disease and/or condition associated with a decrease of ATP7B-dependent lysosomal exocytosis and copper accumulation.

Therefore, in a first aspect the invention relates to a nucleic acid construct (hereinafter also referred as "nucleic acid construct of the invention"), that comprises: a) a nucleotide sequence of the α1-antitrypsin gene (AAT) promoter; b) a nucleotide sequence encoding Copper-transporting ATPase 2 (ATP7B); and c) a polyadenylation signal sequence.

In another aspect, the invention relates to an expression vector (hereinafter also referred as "expression vector of the invention"), that comprises a nucleic acid construct of the invention.

In another aspect, the invention relates to a host cell comprising a nucleic acid construct or an expression vector of the invention.

In another aspect, the invention relates to a viral particle (hereinafter also referred as "viral particle of the invention"), that comprises a nucleic construct or an expression vector of the invention. Preferably, the nucleic acid construct constitutes the genomic sequence of the viral vector.

In another aspect, the invention relates to a pharmaceutical composition that comprises a product of the invention, i.e. a product that comprises a nucleic acid construct of the invention, and a pharmaceutically acceptable carrier. The term "product of the invention" as used herein refers to and indistinctively covers any of: a) the nucleic acid construct of the invention; b) the expression vector of the invention, c) the host cell of the invention and d) the viral particle of the invention.

In another aspect, the invention further relates to a kit comprising a nucleic acid construct, vector, host cell, viral particle or pharmaceutical composition of the invention in one or more containers.

In another aspect, the invention relates to a product of the invention for use in medicine (as a medicament or medicinal composition). This use in medicine includes the treatment of a condition caused by a deficiency or dysfunction of Copper-transporting ATPase 2. Said another way, the invention relates to: the use of a product of the invention in the preparation of a medicament for use in the treatment of a condition caused by a deficiency or dysfunction of Copper-transporting ATPase 2; and to a method for the treatment of a condition caused by a deficiency or dysfunction of Copper-transporting ATPase 2 in a subject or patient, that comprises administering to the subject or patient a therapeutically effective amount of a product of the invention. In a more particular aspect, the product of the invention is used for the treatment of Wilson's disease.

In another aspect, the invention further relates to a pharmaceutical composition comprising a product of the invention as described above, for the proposed uses in medicine and therapeutic methods herein described.

In an even further aspect, the invention relates to a process of producing viral particles of the invention comprising the steps of:
a) culturing a host cell containing a nucleic acid construct or expression vector of the invention in a culture medium; and
b) harvesting the viral particles in the cell culture supernatant and/or inside the cells.

In a related aspect, the present invention relates to the use of the nucleic acid construct of the invention or the expression vector of the invention for the production of viral particles.

BRIEF DESCRIPTION OF THE D WINGS

FIG. 1: Schematic representation of the nucleic acid construct of the vector AAV2-AAT-wtATP7B expressing human ATP7B. The elements of the construct are: a) the alpha-1-antitrypsin gene promoter (AAT), b) nucleotide sequence encoding human ATP7B, c) the polyadenylation signal sequence (pA), and flanking the vector genome d) the inverted terminal repeat sequences of AAV2 (ITRs).

Figure 2:
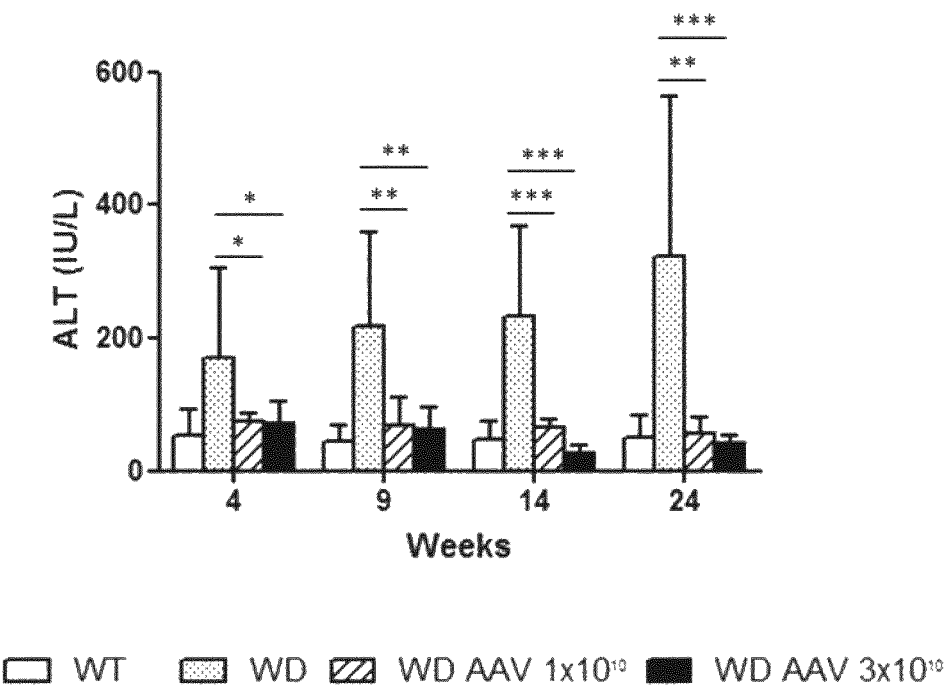

FIG. 2: Serum alanine aminotransferase (ALT) levels in wild type mice (WT), ATP7B deficient mice (Wilson's Disease mice, WD), and WD mice treated with $1\times10^{10}$ vg/mouse (WD AAV $1\times10^{10}$) and with $3\times10^{10}$ vg/mouse (WD AAV $3\times10^{10}$) of the vector AAV2/8-AAT-wtATP7B. Vector was administered when the animals were 6 weeks old. ALT levels were measured 4, 9, 14, and 24 weeks after treatment (Weeks) and is expressed as IU/L (IU: international units). ns: no significant; *: $p<0.05$, : $p<0.01$; *: $p<0.001$ [Mann-Whitney unpaired test].

Figure 3:
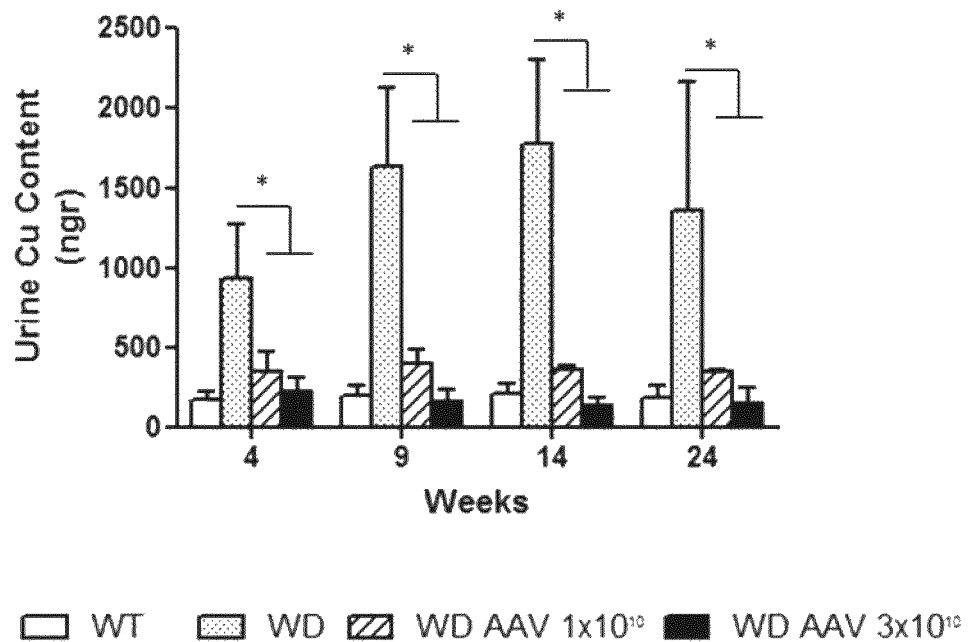

FIG. 3: Total urine copper content in wild type mice (WT), ATP7B deficient mice (Wilson's Disease mice, WD), and WD mice treated with $1\times10^{10}$ vg/mouse (WD AAV $1\times10^{10}$) and with $3\times10^{10}$ vg/mouse (WD AAV $3\times10^{10}$) of the vector AAV2/8-AAT-wtATP7B (n=5 in each group). Copper content was measured 4, 9, 14, and 24 weeks after treatment (Weeks) and is expressed as nanograms of Cu (ngr). ns: no significant; *: $p<0.05$, : $p<0.01$; *: $p<0.001$ [Mann-Whitney unpaired test].

Figure 4:
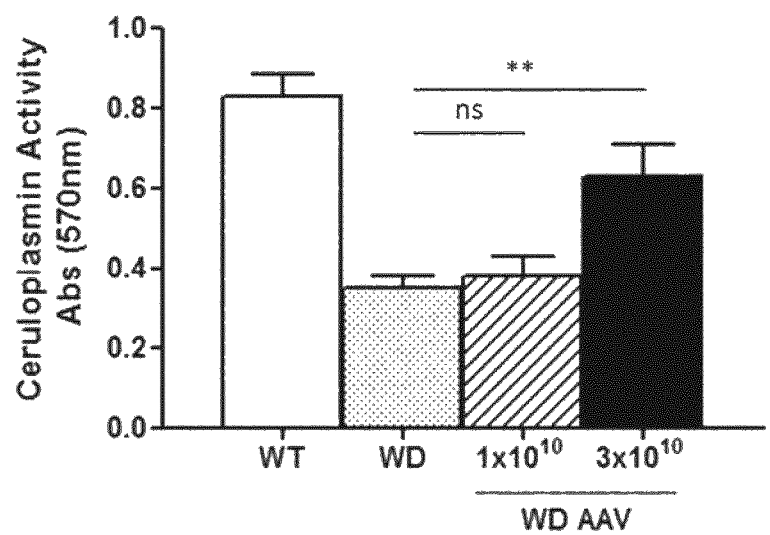

FIG. 4: Serum ceruloplasmin activity in wild type mice (WT), ATP7B deficient mice (Wilson's Disease mice, WD), and WD mice treated with $1\times10^{10}$ vg/mouse (WD AAV $1\times10^{10}$) and with $3\times10^{10}$ vg/mouse (WD AAV $3\times10^{10}$) of the vector AAV2/8-AAT-wtATP7B (n=5 in each group). Ceruloplasmin activity was measured 4 weeks after treatment and is expressed as the absorbance measured at 570 nm of wave length [Abs(570 nm)]. ns: no significant; *: $p<0.05$, : $p<0.01$; *: $p<0.001$ [Mann-Whitney unpaired test].

Figure 5A:
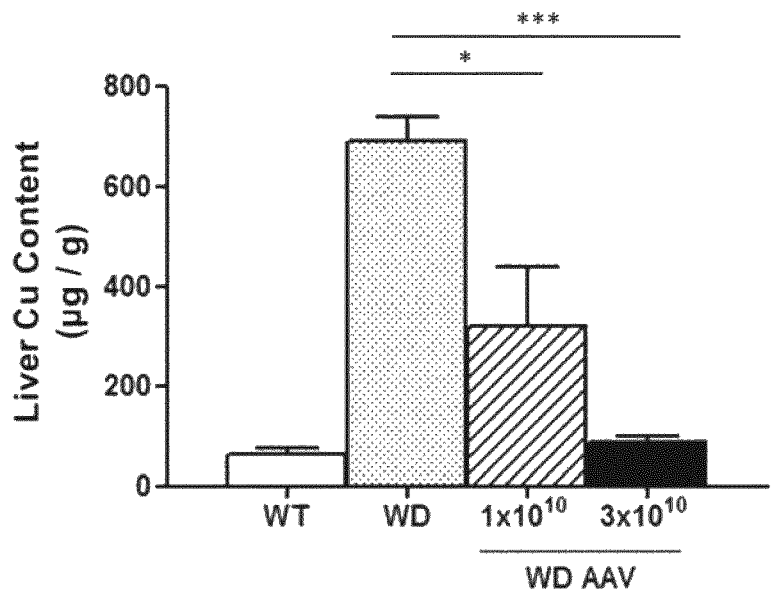

FIG. 5A: Liver Cu content in wild type mice (WT), ATP7B deficient mice (Wilson's Disease mice, WD), and WD mice treated with $1\times10^{10}$ vg/mouse (WD AAV $1\times10^{10}$) and with $3\times10^{10}$ vg/mouse (WD AAV $3\times10^{10}$) of the vector AAV2/8-AAT-wtATP7B (n=5 in each group). Cupper content was determined after sacrificing the animals 24 weeks after treatment (30 weeks of age) by atomic absorption spectroscopy; and is expressed as µg/g (Cu µg/g of dry liver tissue). ns: no significant; *: $p<0.05$, : $p<0.01$; *: $p<0.001$ [Mann-Whitney unpaired test].

Figure 5B:
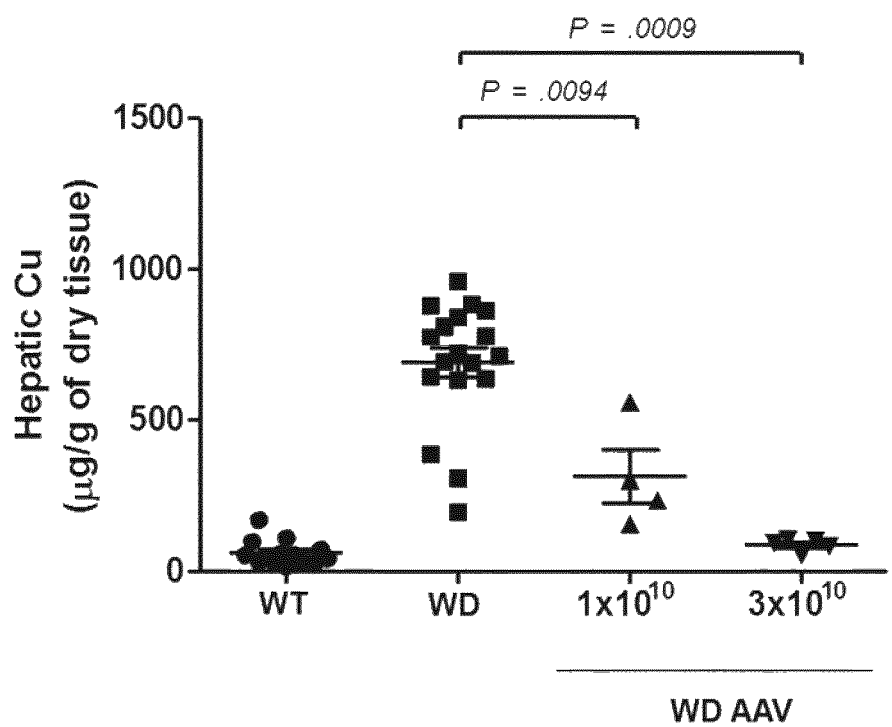

FIG. 5B. Liver Cu content in WT mice (n=15), WD mice (n=25) and WD mice treated with $1\times10^{10}$ vg/mouse (n=5) and with $3\times10^{10}$ vg/mouse (n=5) of the vector AAV2/8-

AAT-wtATP7B as described for FIG. 5A wherein the liver Cu content is presented in individualized form and with the inclusion of more animals in the WD and the WT groups.

Figure 6:
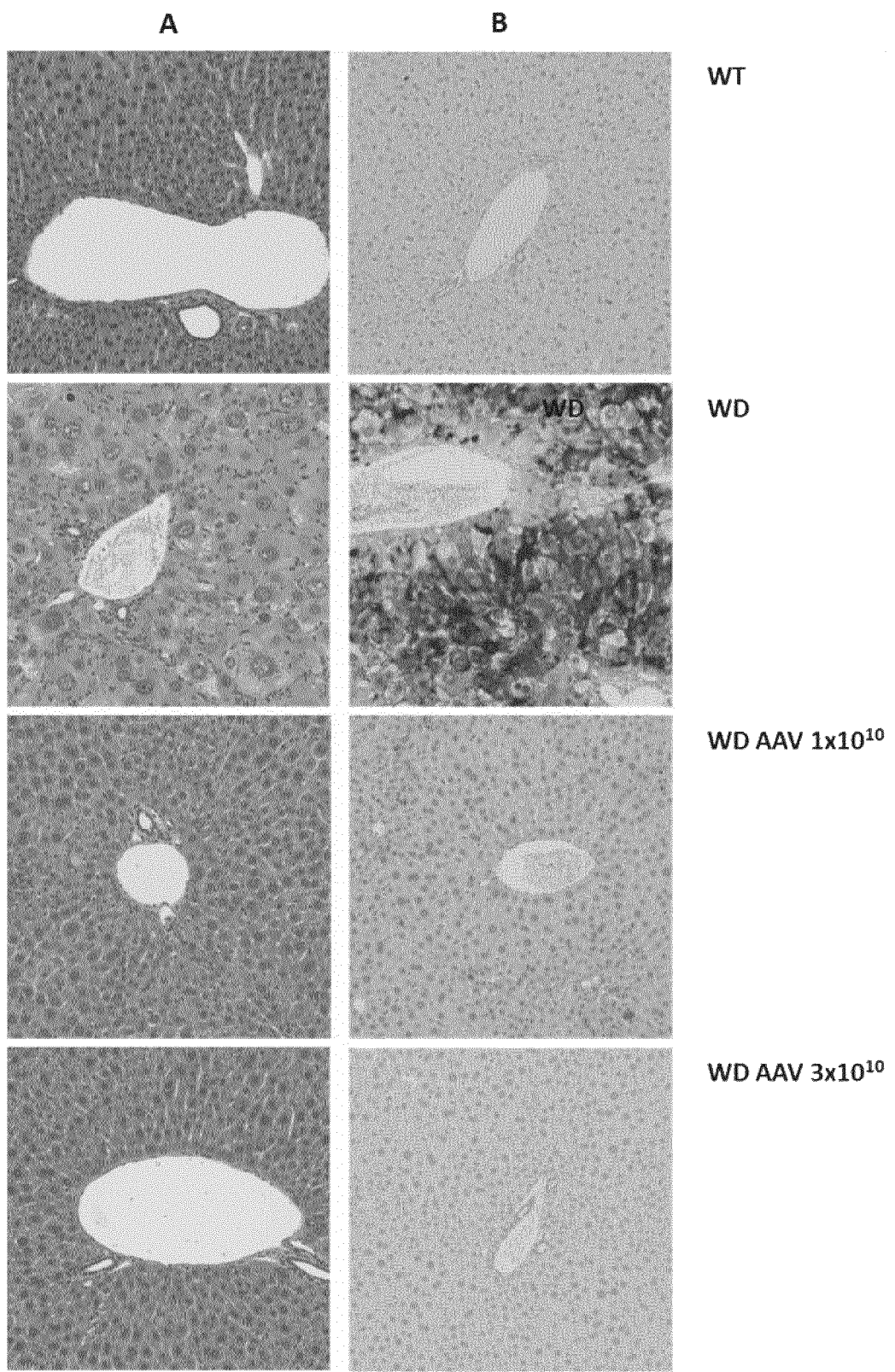

FIG. 6: Histological images of livers of wild type animals (WT), ATP7B deficient mice (Wilson's Disease mice, WD), and WD mice treated with $1 \times 10^{10}$ vg/mouse (WD AAV $1 \times 10^{10}$) and with $3 \times 10^{10}$ vg/mouse (WD AAV $3 \times 10^{10}$) of the vector AAV2/8-AAT-wtATP7B (n=5 in each group). Images were taken after sacrificing the animals (30 weeks of age). A: Images of liver sections stained with hematoxylin and eosin. B: Images of histological samples stained by Timm's sulphide silver technique for detection of copper deposits.

Figure 7:
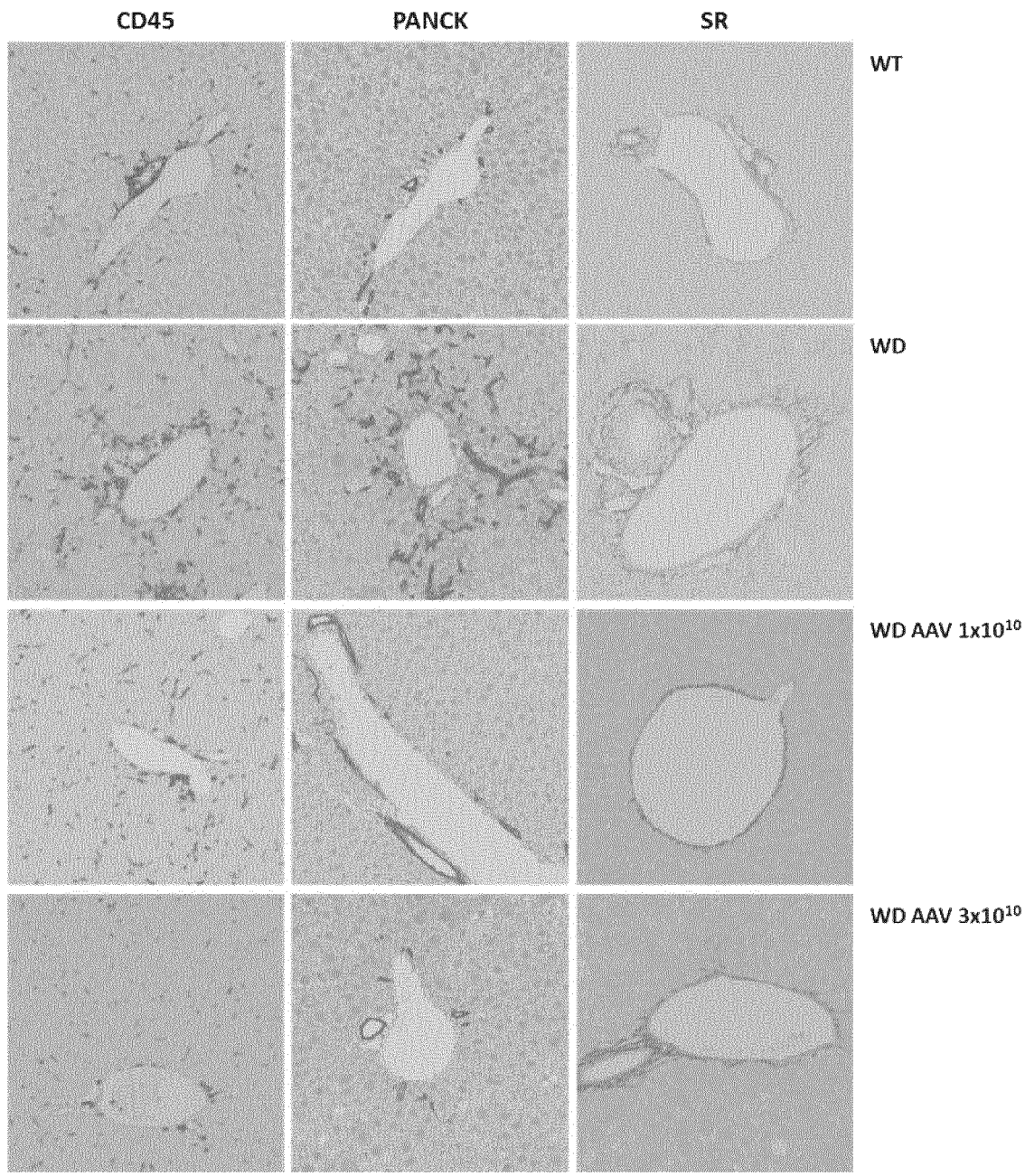

FIG. 7: Analysis of liver inflammation, Bile duct proliferation and fibrosis. Images of livers of wild type animals (WT), ATP7B deficient mice (Wilson's Disease mice, WD), and WD mice treated with $1 \times 10^{10}$ vg/mouse (WD AAV $1 \times 10^{10}$) and with $3 \times 10^{10}$ vg/mouse (WD AAV $3 \times 10^{10}$) of the vector AAV2/8-AAT-wtATP7B (n=5 in each group). Analysis was performed after sacrificing the animals (30 weeks of age). CD45: Images of liver sections immunostained with anti-CD45 for detecting liver inflammatory infiltrates. PANCK: Images of liver sections immunostained with anti-PANCK for detecting bile duct proliferation. SR: Images of liver sections stained with Sirius red for detecting fibrosis.

Figure 8:
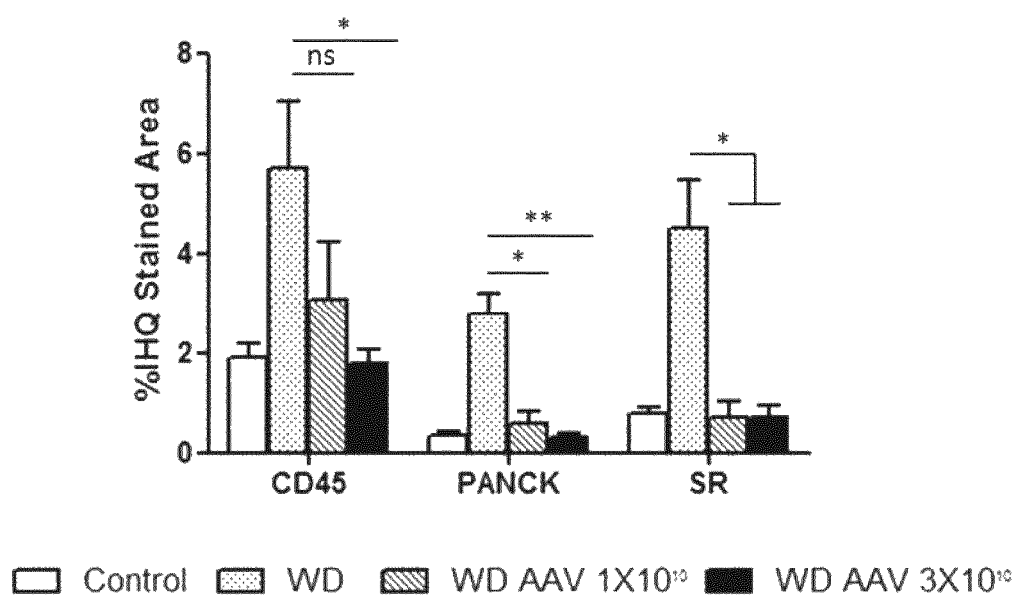

FIG. 8: Graphic representation of the quantitative analysis of liver inflammation, bile duct proliferation, and fibrosis conducted on digital images of liver sections immunostained with anti-CD45 (CD45; as inflammatory marker), or with anti-PanCk (PANCK; as bile duct proliferation marker); or stained with Sirius Red (SR; as fibrosis marker). Measurements are expressed as the ratio of immuno-histochemically stained area, Sirius Red stained area in the case of fibrosis, with respect to the total area (% IHQ Stained Area). ns: no significant; *: $p<0.05$, : $p<0.01$; *: $p<0.001$ [Mann-Whitney unpaired test].

FIG. 9: Feces copper concentration (A) and urine copper concentration (B) in WD mice (WD) (n=5), WD mice treated with $3 \times 10^{10}$ vg/mouse (WD AAV) (n=5) of the vector AAV2/8-AAT-wtATP7B, and in a group of heterozygous littermates (Control). 2 weeks after treatment half of the mice in each group received a copper overload by intraperitoneal administration of 100 μg (+CuSO$_4$); and the other half were left untreated (−CuSO$_4$). Copper concentration was analyzed in feces (A) and urine (B) collected during the next 24 hours.

Figure 10:
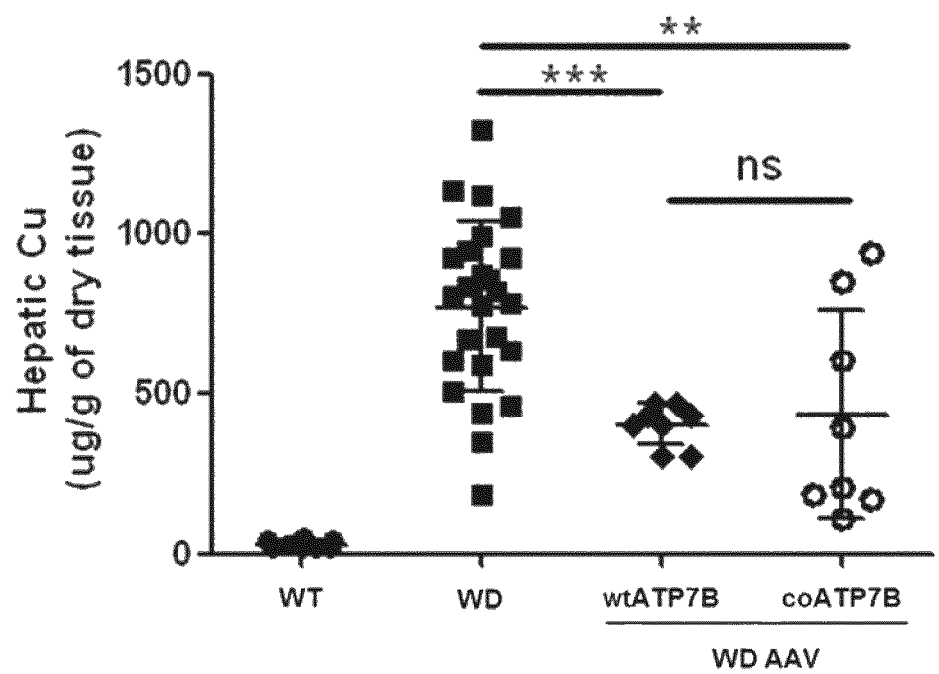

FIG. 10. Liver Cu content in wild type mice (WT) (n=15), WD mice (n=25), WD mice treated with $1 \times 10^{10}$ vg/mouse (n=8) (suboptimal dose) of the vector AAV2/8-AAT-wtATP7B (ATP7B), and. WD mice treated with $1 \times 10^{10}$ vg/mouse (n=8) of the vector AAV2/8-AAT-coATP7B (coATP7B). Cupper content was determined after sacrificing the animals 24 weeks after treatment by atomic absorption spectroscopy; and is expressed as μg/g (Cu μg/g of dry liver tissue). ns: no significant; *: $p<0.05$, : $p<0.01$; *: $p<0.001$ [Mann-Whitney unpaired test].

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The terms "nucleic acid sequence" and "nucleotide sequence" may be used interchangeably to refer to any molecule composed of or comprising monomeric nucleotides. A nucleic acid may be an oligonucleotide or a polynucleotide. A nucleotide sequence may be a DNA or RNA. A nucleotide sequence may be chemically modified or artificial. Nucleotide sequences include peptide nucleic acids (PNA), morpholinos and locked nucleic acids (LNA), as well as glycol nucleic acids (GNA) and threose nucleic acid (TNA). Each of these sequences is distinguished from naturally-occurring DNA or RNA by changes to the backbone of the molecule. Also, phosphorothioate nucleotides may be used. Other deoxynucleotide analogs include methylphosphonates, phosphoramidates, phosphorodithioates, N3'P5'-phosphoramidates and oligoribonucleotide phosphorothioates and their 2'-0-allyl analogs and 2'-0-methylribonucleotide methylphosphonates which may be used in a nucleotide of the invention.

The term "nucleic acid construct" as used herein refers to a man-made nucleic acid molecule resulting from the use of recombinant DNA technology. A nucleic acid construct is a nucleic acid molecule, either single- or double-stranded, which has been modified to contain segments of nucleic acids sequences, which are combined and juxtaposed in a manner, which would not otherwise exist in nature. A nucleic acid construct usually is a "vector", i.e. a nucleic acid molecule which is used to deliver exogenously created DNA into a host cell.

The term "expression vector" or "vector" as used herein refers to a recombinant nucleotide sequence that is capable of effecting expression of a gene (transgene) in host cells or host organisms compatible with such sequences. Together with the transgene, expression vectors typically include at least suitable transcription regulatory sequences and optionally, 3' transcription termination signals. Additional factors necessary or helpful in effecting expression may also be present, such as expression enhancer elements able to respond to a precise inductive signal (endogenous or chimeric transcription factors) or specific for certain cells, organs or tissues.

The term "subject" or "patient" as used herein, refers to mammals. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

The term "packaging cells" as used herein, refers to a cell or cell line which may be transfected with a helper vector or virus or a DNA construct, and provides in trans all the missing functions which are required for the complete replication and packaging of a viral vector. Typically, the packaging cells express in a constitutive or inducible manner one or more of said missing viral functions.

A Nucleic Acid Construct of the Invention
Nucleotide Sequence of the α1-Antitrypsin Gene (AAT) Promoter As used herein, the term "eukaryotic promoter" refers to a DNA sequence region that initiates transcription of a particular gene, or one or more coding sequences, in eukaryotic cells. A promoter can work in concert with other regulatory regions or elements to direct the level of transcription of the gene or coding sequence/s. These regulatory elements include, without limitation, transcription factor binding sites, repressor and activator protein binding sites, and any other sequences of nucleotides known to one of skill in the art to act directly or indirectly to regulate the amount of transcription from the promoter, including e.g. attenuators, enhancers, and silencers. The promoter is located near the transcription start site of the gene or coding sequence to which is operably linked, on the same strand and upstream of the DNA sequence (towards the 5' region of the sense strand). A promoter can be about 100-1000 base pairs long. Positions in a promoter are designated relative to the transcriptional start site for a particular gene (i.e., positions upstream are negative numbers counting back from −1, for example −100 is a position 100 base pairs upstream).

The term "core promoter" or "minimal promoter" refers to the minimal portion of a promoter sequence required to properly initiate transcription. It includes the transcription start site (TSS) and elements directly upstream; a binding site for RNA polymerase (RNA polymerase II); and general transcription factors binding sites. Commonly a promoter also comprises a proximal promoter sequence (upstream of the core promoter), that contains other primary regulatory elements (such as enhancers, silencers, boundary elements/insulators); and a distal promoter sequence (downstream of core promoter), that may contain additional regulatory elements, normally with a weaker influence on the level of transcription of the gene.

The nucleic acid construct of the invention comprises the nucleotide sequence of the α1-antitrypsin (AAT) gene promoter, i.e. it comprises the sequence of the core promoter of the gene. In one embodiment, optionally in combination with one or more features of the various embodiments described above or below, the nucleic acid of the invention comprises the sequence of the core promoter of the AAT gene as the only eukaryotic regulatory element sequence.

In one embodiment, optionally in combination with one or more features of the various embodiments described above or below, the sequence of the AAT promoter is the partial sequence delimited by bases 156 . . . 460 of SEQ.ID.NO.1.

According to the invention, the AAT promoter sequence is operably linked to the nucleotide sequence encoding Copper-transporting ATPase 2. As used herein, the term "operably linked" refers to a linkage of polynucleotide (or polypeptide) elements in a functional relationship. A nucleic acid is "operably linked" when it is placed into a functional relationship with another nucleic acid sequence. For instance, a promoter or transcription regulatory sequence is operably linked to a coding sequence if it affects the transcription of the coding sequence. Operably linked means that the DNA sequences being linked are typically contiguous; where it is necessary to join two protein encoding regions, they are contiguous and in reading frame.

Copper-Transporting ATPase 2 (ATP7B)

Copper-transporting ATPase 2 (ATP7B) is a P-type cation transport ATPase that functions exporting copper out of the cells.

The gene that encodes human enzyme is located at chromosome 13 (chromosome location 13q14.3; gene name ATP7B). Information on human ATP7B polypeptide (amino acid sequences, structure, domains and other features) is for example available at Uniprot with Accession number: P35670 (Entry version 168 (03 Sep. 2014), Sequence version 4 (16 Jun. 2009)). Information on the ATP7B gene encoding this enzyme is available at Entrez with accession number Gene ID: 540. 4 isoforms produced by alternative splicing have been described for ATP7B; isoform 1 (identifier P35670-1, 1465 amino acids long) is chosen as the canonical sequence.

In one embodiment, optionally in combination with one or more features of the various embodiments described above or below, the nucleotide acid construct of the invention comprises a nucleotide sequence that encodes a human ATP7B, preferably a human ATP7B whose amino acid sequence is the canonical sequence (SEQ.ID.NO.3), herein also referred to as wtATP7B.

Because of the codons redundancy, there are numerous nucleotide sequences that can be generated encoding ATP7B polypeptides with same amino acids sequence.

In one embodiment, optionally in combination with one or more features of the various embodiments described above or below, the nucleotide sequence encoding the Copper-transporting ATPase 2 is the coding sequence CDS of the SEQ.ID.NO.1, bases 473 . . . 4870.

In one embodiment, optionally in combination with one or more features of the various embodiments described above or below, the nucleotide sequence encoding the Copper-transporting ATPase 2 is the coding sequence CDS of the SEQ.ID.NO.2, bases 473 . . . 4870, a sequence with an optimized codon usage bias for the human cells that encodes the same wtATP7B.

In one embodiment, optionally in combination with one or more features of the various embodiments described above or below, the nucleotide sequence encoding the Copper-transporting ATPase 2 is a sequence wherein at least 1170, at least 1245, at least 1315, or at least 1390 of the codons encoding Copper-transporting ATPase 2 are identical to the coding sequence CDS 473 . . . 4870 of the SEQ.ID.NO.2.

Polyadenylation Signal Sequence

As used herein, the term "polyadenylation signal" or "poly(A) signal" refers to a specific recognition sequence within 3' untranslated region (3' UTR) of the gene, which is transcribed into precursor mRNA molecule and guides the termination of the gene transcription. Poly(A) signal acts as a signal for the endonucleolytic cleavage of the newly formed precursor mRNA at its 3'-end, and for the addition to this 3'-end of a RNA stretch consisting only of adenine bases (polyadenylation process; poly(A) tail). Poly(A) tail is important for the nuclear export, translation, and stability of mRNA. In the context of the invention, the polyadenylation signal is a recognition sequence that can direct polyadenylation of mammalian genes and/or viral genes, in mammalian cells.

Poly(A) signals typically consist of a) a consensus sequence AAUAAA, which has been shown to be required for both 3'-end cleavage and polyadenylation of premessenger RNA (pre-mRNA) as well as to promote downstream transcriptional termination, and b) additional elements upstream and downstream of AAUAAA that control the efficiency of utilization of AAUAAA as a poly(A) signal. There is considerable variability in these motifs in mammalian genes.

In one embodiment, optionally in combination with one or more features of the various embodiments described above or below, the polyadenylation signal sequence of the nucleic acid construct of the invention is a polyadenylation signal sequence of a mammalian gene or a viral gene. Suitable polyadenylation signals include, among others, a SV40 early polyadenylation signal, a SV40 late polyadenylation signal, a HSV thymidine kinase polyadenylation signal, a protamine gene polyadenylation signal, an adenovirus 5 EIb polyadenylation signal, a growth hormone polyadenylation signal, a PBGD polyadenylation signal and the like.

In one embodiment, optionally in combination with one or more features of the various embodiments described above or below, the polyadenylation signal sequence of the nucleic acid construct is a synthetic poly(A) signal sequence which is also capable of directing and effecting the endonucleolytic cleavage and polyadenylation of the precursor mRNA resulting from the transcription of nucleotide sequence coding for ATP7B.

In one embodiment, optionally in combination with one or more features of the various embodiments described above or below, the polyadenylation signal sequence of the nucleic acid construct is the synthetic poly(A) signal sequence delimited by bases 4877 . . . 4932 of the SEQ.ID.NO.1.

Other Nucleotide Elements

In one embodiment, the nucleic acid construct of the invention constitutes the recombinant genome of an expression vector for gene therapy, the expression vector of the invention; and more particularly of a viral vector for gene therapy.

Thus, in one embodiment, optionally in combination with one or more features of the various embodiments described above or below, the nucleic acid construct of the invention further comprises a 5'ITR and a 3'ITR of a virus.

As used herein the term "inverted terminal repeat (ITR)" refers to a nucleotide sequence located at the 5'-end (5'ITR) and a nucleotide sequence located at the 3'-end (3'ITR) of a virus, that contain palindromic sequences and that can fold over to form T-shaped hairpin structures that function as primers during initiation of DNA replication. They are also needed for viral genome integration into host genome; for the rescue from the host genome; and for the encapsidation of viral nucleic acid into mature virions. The ITRs are required in cis for the vector genome replication and its packaging into the viral particles.

In one embodiment, the nucleic acid construct comprises a 5'ITR, a ψ packaging signal, and a 3'ITR of a virus. "ψ packaging signal" is a cis-acting nucleotide sequence of the virus genome, which in some viruses (e.g. adenoviruses, lentiviruses . . . ) is essential for the process of packaging the virus genome into the viral capsid during replication.

In one embodiment, optionally in combination with one or more features of the various embodiments described above or below, the nucleic acid construct comprises a 5'ITR and a 3'ITR of a virus selected from the group consisting of parvoviruses (in particular adeno-associated viruses), adenoviruses, alphaviruses, retroviruses (in particular gamma retroviruses, and lentiviruses), herpesviruses, and SV40; in a preferred embodiment the virus is an adeno-associated virus (AAV), an adenovirus (Ad), or a lentivirus.

In one embodiment, optionally in combination with one or more features of the various embodiments described above or below, the nucleic acid construct comprises a 5'ITR and a 3'ITR of an AAV.

The AAV genome is composed of a linear, single-stranded DNA molecule which contains 4681 bases (Berns and Bohenzky, (1987) Advances in Virus Research (Academic Press, Inc.) 32:243-307). The genome includes inverted terminal repeats (ITRs) at each end which function in cis as origins of DNA replication and as packaging signals for the virus. The ITRs are approximately 145 bp in length. The internal non-repeated portion of the genome includes two large open reading frames, known as the AAV rep and cap genes, respectively. These genes code for the viral proteins involved in replication and packaging of the virion. In particular, at least four viral proteins are synthesized from the AAV rep gene, Rep 78, Rep 68, Rep 52 and Rep 40, named according to their apparent molecular weight. The AAV cap gene encodes at least three proteins, VP1, VP2 and VP3. For a detailed description of the AAV genome, see, e.g., Muzyczka, N. (1992) Current Topics in Microbiol. and Immunol. 158:97-129.

The construction of recombinant AAV virions is generally known in the art and has been described for instance in U.S. Pat. No. 5,173,414 and U.S. Pat. No. 5,139,941; WO 92/01070, WO 93/03769, (Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

In a preferred embodiment, optionally in combination with one or more features of the various embodiments described above or below, the nucleic acid construct or the expression vector of the invention comprises or consists of:
  a) a nucleotide sequence of the α1-antitrypsin gene (AAT) promoter;
  b) a nucleotide sequence encoding a Copper-transporting ATPase 2;
  c) a polyadenylation signal sequence; and
  d) a 5'ITR and a 3'ITR sequences of an adeno-associated virus (AAV.

The invention may be carried out by using ITRs of any AAV serotype, including AAV1, AAV2, AAV3 (including types 3A and 3B), AAV4, AAV5, AAV6, AAV7, AAV8, AAV9, AAV10, AAV11, AAV12, avian AAV, bovine AAV, canine AAV, equine AAV, ovine AAV, and any other AAV serotype now known or later discovered.

In one embodiment, optionally in combination with one or more features of the various embodiments described above or below, the nucleic acid construct comprises a 5'ITR and a 3'ITR of an AAV of a serotype selected from the group consisting of an AAV1, an AAV2, and an AAV4. In a preferred embodiment the nucleic acid construct comprises the ITR sequences delimited by bases 1 . . . 141, and bases 4968 . . . 5107 of SEQ.ID.NO.1, that are the ITRs sequences of an AAV2.

The ITRs are the only AAV viral elements which are required in cis for the AAV genome replication and its packaging into the viral particles.

In one embodiment, optionally in combination with one or more features of the various embodiments described above or below, the nucleic acid construct comprises a 5'ITR, a ψpackaging signal, and a 3'ITR of an adenovirus of any of the serotypes within any of the classification subgroups (A-F). In a particular embodiment, optionally in combination with one or more features of the various embodiments described above or below, these 5'ITR, ψ signal, and 3'ITR sequences come from a sub-group C adenovirus, more preferably from an adenovirus of serotype 2 (Ad2) or serotype 5 (Ad5).

On the other hand, in other embodiments the invention can be carried out by using synthetic 5'ITR and/or 3'ITR; and also by using a 5'ITR and a 3'ITR which come from viruses of different serotype.

All other viral genes required for viral vector replication can be provided in trans within the virus-producing cells (packaging cells) as described below. Therefore, their inclusion in the nucleic acid construct of a viral vector genome according to the invention is optional. In one embodiment, optionally in combination with one or more features of the various embodiments described above or below, the expression vector is an AAV vector.

In a particular embodiment, the nucleic acid construct of the invention constitutes an AAV vector whose nucleotide sequence is the SEQ.ID.NO.1 or the SEQ.ID.NO.2.

In another embodiment, optionally in combination with one or more features of the various embodiments described above or below, the expression vector is an adenoviral vector. This adenoviral vector according to the invention can be, in particular, a first-, second-, or third-generation adenovirus [see Adenovirus. Methods and Protocols. Chillón M. and Bosch A. (Eds); third Edition; 2014 Springer], or any other adenoviral vector system already known or later described.

In a particular embodiment, optionally in combination with one or more features of the various embodiments described above or below, the viral vector of the invention is a "third generation adenovirus", which may also be referred to as "gutless adenovirus", "helper-dependent adenovirus (HD-Ad)", or "high capacity adenovirus (HC-Ad)". A third generation adenovirus has all viral coding regions removed (gutless); it depends on a helper adenovirus to replicate (helper-dependent); and it can carry and deliver into the host cell up to 36 Kbp inserts of foreign genetic material (high-capacity). A gutless adenovirus keeps the inverted terminal repeats ITRs (5' and 3') and the packaging signal (y).

The nucleic acid construct and expression vector of the invention herein described can be prepared and obtained by conventional methods known to those skilled in the art: Sambrook and Russell (Molecular Cloning: a Laboratory Manual; Third Edition; 2001 Cold Spring Harbor Laboratory Press); and Green and Sambrook (Molecular Cloning: a Laboratory Manual; Fourth Edition; 2012 Cold Spring Harbor Laboratory Press).

A Viral Particle of the Invention for Gene Therapy

The terms "viral particle", and "virion" are used herein interchangeably and relate to an infectious and typically replication-defective virus particle comprising the viral genome (i.e. the nucleic acid construct of the expression viral vector) packaged within a capsid and, as the case may be, a lipidic envelope surrounding the capsid.

In one embodiment, optionally in combination with one or more features of the various embodiments described above or below, the virion of the invention is a "recombinant AAV virion" or "rAAV virion" obtained by packaging of a nucleic acid construct of an AAV vector according to the invention in a protein shell.

Proteins of the viral capsid of an adeno-associated virus (capsid proteins VP1, VP2, and VP3) are generated from a single viral gene (cap gene). Differences among the capsid protein sequences of the various AAV serotypes result in the use of different cell surface receptors for cell entry. In combination with alternative intracellular processing pathways, this gives rise to distinct tissue tropisms for each AAV serotype.

In a particular embodiment, a recombinant AAV virion according to the invention may be prepared by encapsidating the nucleic acid construct of an AAV genome derived from a particular AAV serotype on a viral particle formed by natural Cap proteins corresponding to an AAV of the same particular serotype. Nevertheless, several techniques have been developed to modify and improve the structural and functional properties of naturally occurring AAV viral particles (Bunning H et al. *J Gene Med* 2008; 10: 717-733). Thus, in another AAV viral particle according to the invention the nucleotide construct of the viral vector flanked by ITR(s) of a given AAV serotype can be packaged, for example, into: a) a viral particle constituted of capsid proteins derived from a same or different AAV serotype [e.g. AAV2 ITRs and AAV5 capsid proteins; AAV2 ITRs and AAV8 capsid proteins; etc]; b) a mosaic viral particle constituted of a mixture of capsid proteins from different AAV serotypes or mutants [e.g. AAV2 ITRs with AAV1 and AAV5 capsid proteins]; c) a chimeric viral particle constituted of capsid proteins that have been truncated by domain swapping between different AAV serotypes or variants [e.g. AAV2 ITRs with AAV5 capsid proteins with AAV3 domains]; or d) a targeted viral particle engineered to display selective binding domains, enabling stringent interaction with target cell specific receptors [e.g. AAV4 ITRs with AAV2 capsid proteins genetically truncated by insertion of a peptide ligand; or AAV2 capsid proteins non-genetically modified by coupling of a peptide ligand to the capsid surface].

The skilled person will appreciate that the AAV virion according to the invention may comprise capsid proteins of any AAV serotype. In one embodiment, optionally in combination with one or more features of the various embodiments described above or below, the viral particle comprises capsid proteins of an AAV. In a particular embodiment, optionally in combination with one or more features of the various embodiments described above or below, the AAV viral particle comprises capsid proteins from a serotype selected from the group consisting of an AAV1, an AAV5, an AAV7, an AAV8, and an AAV9 which are more suitable for delivery to the liver cells (Nathwani et al. *Blood* 2007; 109: 1414-1421; Kitajima et al. *Atherosclerosis* 2006; 186:65-73). In a particular embodiment, optionally in combination with one or more features of the various embodiments described above or below, the viral particle comprises a nucleic acid construct of the invention wherein the 5'ITR and 3'ITR sequences of the nucleic acid construct are of an AAV2 serotype and the capsid proteins are of an AAV8 serotype. In a particular embodiment, optionally in combination with one or more features of the various embodiments described above or below, the AAV viral particle comprises at least a capsid protein from Anc80, a predicted ancestor of viral AAVs serotypes 1, 2, 8, and 9 that behaves as a highly potent gene therapy vector for targeting liver, muscle and retina (Zinn et al. *Cell Reports* 2015; 12:1-13). In a more particular embodiment, the viral particle comprises the Anc80L65 VP3 capsid protein (Genbank accession number: KT235804).

Viral-glycan interactions are critical determinants of host cell invasion. In a particular embodiment, optionally in combination with one or more features of the various embodiments described above or below, the AAV viral particle comprises capsid proteins comprising one or more amino acids substitutions, wherein the substitutions introduce a new glycan binding site or a new heparan sulfate (HS) binding site into the AAV capsid protein. In a more particular embodiment, the amino acid substitutions are in amino acid 266, amino acids 463-475 and amino acids 499-502 in AAV2 or the corresponding amino acid positions in AAV1, AAV3, AAV4, AAV5, AAV6, AAV7, AAV8, AAV9, AAV10 or any other AAV serotype, also included Anc80 and Anc80L65.

The introduced new glycan binding site can be a hexose binding site [e.g. a galactose (Gal), a mannose (Man), a glucose (Glu) or a fucose (fuc) binding site]; a sialic acid (Sia) binding site [e.g. a Sia residue such as is N-acetylneuraminic acid (NeuSAc) or N-Glycolylneuraminic acid (NeuSGc)]; or a disaccharide binding site, wherein the disaccharide is a sialic acid linked to galactose, for instance in the form of Sia(alpha2,3)Gal or Sia(alpha2,6)Gal. Detailed guidance to introduce a new binding site from an AAV serotype into a capsid protein of an AAV of another serotype is given on international patent publication WO2014144229 and in Shen et al. (J. Biol Chem. 2013; 288(40):28814-28823). In a particular embodiment, optionally in combination with one or more features of the various embodiments described above or below, the Gal binding site from AAV9 is introduced into the AAV2 VP3 backbone resulting in a dual glycan-binding AAV strain which is able to use both HS and Gal receptors for cell entry. Preferably, said dual glycan-binding AAV strain is AAV2G9. Shen et al. generated AAV2G9 by substituting amino acid residues directly involved and immediately flanking the Gal recognition site on the AAV9 VP3 capsid protein subunit onto corresponding residues on the AAV2 VP3 subunit coding region (AAV2 VP3 numbering Q464V, A467P, D469N, I470M, R471A, D472V, S474G, Y500F, and S501A).

In another embodiment, optionally in combination with one or more features of the various embodiments described above or below, the virion of the invention is an adenoviral virion, such as an Ad5 virion. As it is the case for AAV virions, the capsid proteins of Ad virions can also be engineered to modify their tropism and cellular targeting properties.

Production of Viral Particles

Production of viral particles carrying the nucleic acid construct of the expression viral vector of the invention can be performed by means of conventional methods and protocols, which are selected having into account the structural features chosen for the actual embodiment of the nucleic acid construct and viral particle of the vector to be produced. Briefly, viral particles can be produced in a specific virus-producing cell (packaging cell) which is transfected with the nucleic acid construct of the vector to be packaged, in the presence of a helper vector or virus or other DNA construct(s).

Accordingly, in one aspect the invention concerns the use of the nucleic acid construct or expression vector of the invention for the production of viral particles.

In a related aspect, the invention concerns a process of producing viral particles of the invention comprising the steps of:

a) culturing a host cell comprising a nucleic acid construct or expression vector of the invention in a culture medium; and b) harvesting the viral particles from the cell culture supernatant and/or inside the cells.

Preferably, said host cell is a packaging cell as described below. Suitable culture media will be known to a person skilled in the art. The ingredients that compose such media may vary depending on the type of cell to be cultured. In addition to nutrient composition, osmolarity and pH are considered important parameters of culture media. The cell growth medium comprises a number of ingredients well known by the person skilled in the art, including amino acids, vitamins, organic and inorganic salts, sources of carbohydrate, lipids, trace elements ($CuSO_4$, $FeSO_4$, $Fe(NO_3)_3$, $ZnSO_4$ . . . ), each ingredient being present in an amount which supports the cultivation of a cell in vitro (i.e., survival and growth of cells). Ingredients may also include different auxiliary substances, such as buffer substances (like sodium bicarbonate, Hepes, Tris . . . ), oxidation stabilizers, stabilizers to counteract mechanical stress, protease inhibitors, animal growth factors, plant hydrolyzates, anti-clumping agents, anti-foaming agents. Characteristics and compositions of the cell growth media vary depending on the particular cellular requirements. Examples of commercially available cell growth media are: MEM (Minimum Essential Medium), BME (Basal Medium Eagle) DMEM (Dulbecco's modified Eagle's Medium), Iscoves DMEM (Iscove's modification of Dulbecco's Medium), GMEM, RPMI 1640, Leibovitz L-15, CHO, McCoy's, Medium 199, HEK293, Ham (Ham's Media) F10 and derivatives, Ham F12, DMEM/F12, etc.

A Host Cell of the Invention

In another aspect, the invention relates to a host cell comprising a nucleic acid construct or expression vector of the invention.

The term "host cell" as used herein refers to any cell line that is susceptible to infection by a virus of interest, and amenable to culture in vitro.

The host cell of the invention may be used for ex vivo gene therapy purposes. In such embodiments, the cells are transfected with the nucleic acid construct or viral vector of the invention and subsequently transplanted to the patient or subject. Transplanted cells can have an autologous, allogenic or heterologous origin. For clinical use, cell isolation will generally be carried out under Good Manufacturing Practices (GMP) conditions. Before transplantation, cell quality and absence of microbial or other contaminants is typically checked and liver preconditioning, such as with radiation and/or an immunosuppressive treatment, may be carried out. Furthermore, the host cells may be transplanted together with growth factors to stimulate cell proliferation and/or differentiation, such as Hepatocyte Growth Factor (HGF).

In a particular embodiment, the host cell is used for ex vivo gene therapy into the liver. Preferably, said cells are eukaryotic cells such as mammalian cells, these include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. A person skilled in the art will choose the more appropriate cells according to the patient or subject to be transplanted.

Said host cell may be a cell with self-renewal and pluripotency properties, such as stem cells or induced pluripotent stem cells. Stem cells are preferably mesenchymal stem cells. Mesenchymal stem cells (MSCs) are capable of differentiating into at least one of an osteoblast, a chondrocyte, an adipocyte, or a myocyte and may be isolated from any type of tissue. Generally MSCs will be isolated from bone marrow, adipose tissue, umbilical cord, or peripheral blood. Methods for obtaining thereof are well known to a person skilled in the art. Induced pluripotent stem cells (also known as iPS cells or iPSCs) are a type of pluripotent stem cell that can be generated directly from adult cells. Yamanaka et al. induced iPS cells by transferring the Oct3/4, Sox2, Klf4 and c-Myc genes into mouse and human fibroblasts, and forcing the cells to express the genes (WO 2007/069666). Thomson et al. subsequently produced human iPS cells using Nanog and Lin28 in place of Klf4 and c-Myc (WO 2008/118820).

Said host cells may also be hepatocytes. Hepatocyte transplantation procedures, including cell isolation and subsequent transplantation into a human or mice recipient is described for instance in Filippi and Dhawan, Ann NY Acad Sci. 2014, 1315 50-55; Yoshida et al., Gastroenterology 1996, 111: 1654-1660; Irani et al. Molecular Therapy 2001, 3:3, 302-309; and Vogel et al. J Inherit Metab Dis 2014, 37:165-176. A method for ex vivo transduction of a viral vector into hepatocytes is described for instance in Merle et al., Scandinavian Journal of Gastroenterology 2006, 41:8, 974-982.

In another particular embodiment, the host cell is a packaging cell. Said cells can be adherent or suspension cells. The packaging cell, and helper vector or virus or DNA construct(s) provide together in trans all the missing functions which are required for the complete replication and packaging of the viral vector.

Preferably, said packaging cells are eukaryotic cells such as mammalian cells, including simian, human, dog and rodent cells. Examples of human cells are PER.C6 cells (WO01/38362), MRC-5 (ATCC CCL-171), WI-38 (ATCC CCL-75), HEK-293 cells (ATCC CRL-1573), HeLa cells (ATCC CCL2), and fetal rhesus lung cells (ATCC CL-160). Examples of non-human primate cells are Vero cells (ATCC CCL81), COS-1 cells (ATCC CRL-1650) or COS-7 cells (ATCC CRL-1651). Examples of dog cells are MDCK cells (ATCC CCL-34). Examples of rodent cells are hamster cells, such as BHK21-F, HKCC cells, or CHO cells.

As an alternative to mammalian sources, cell lines for use in the invention may be derived from avian sources such as chicken, duck, goose, quail or pheasant. Examples of avian cell lines include avian embryonic stem cells (WO01/85938 and WO03/076601), immortalized duck retina cells (WO2005/042728), and avian embryonic stem cell derived cells, including chicken cells (WO2006/108846) or duck cells, such as EB66 cell line (WO2008/129058 & WO2008/142124).

In another embodiment, said host cell are insect cells, such as SF9 cells (ATCC CRL-1711), Sf21 cells (IPLB-Sf21), MG1 cells (BTI-TN-MG1) or High Five™ cells (BTI-TN-5B1-4).

Accordingly, in a particular embodiment, optionally in combination with one or more features of the various embodiments described above or below, the host cell comprises:
 a) a nucleic acid construct or expression vector of the invention (i.e., the recombinant AAV genome), generally as a plasmid;
 b) a nucleic acid construct, generally a plasmid, encoding AAV rep and/or cap genes which does not carry the ITR sequences; and/or
 c) a nucleic acid, generally a plasmid or virus, construct comprising viral helper genes.

Viral genes necessary for AAV replication are referred herein as viral helper genes. Typically, said genes necessary for AAV replication are adenoviral helper genes, such as E1A, E1B, E2a, E4, or VA RNAs. Preferably, the adenoviral helper genes are of the Ad5 or Ad2 serotype.

Conventional methods can be used to produce viral particles of the AAV vector, which consist on transient cell co-transfection with a nucleic acid construct (e.g. a plasmid) carrying the recombinant AAV vector/genome of the invention; a nucleic acid construct (e.g., an AAV helper plasmid) that encodes rep and cap genes, but does not carry ITR sequences; and with a third nucleic acid construct (e.g., a plasmid) providing the adenoviral functions necessary for AAV replication. Thus, in a particular embodiment, optionally in combination with one or more of the features of the various embodiments described above or below, said host cell is characterized by comprising:
 i) a nucleic acid construct or an expression vector of the invention (i.e., the recombinant AAV genome);
 ii) a nucleic acid construct encoding AAV rep and cap genes which does not carry the ITR sequences; and
 iii) a nucleic acid construct comprising adenoviral helper genes.

Alternatively, the rep, cap, and adenoviral helper genes can be combined on a single plasmid (Blouin V et al. *J Gene Med.* 2004; 6(suppl): S223-S228; Grimm D. et al. *Hum. Gene Ther.* 2003; 7: 839-850). Thus, in another particular embodiment, optionally in combination with one or more of the features of the various embodiments described above or below, said host cell is characterized by comprising:
 i) a nucleic acid construct or an expression vector of the invention (i.e., the recombinant AAV genome); and
 ii) a plasmid encoding AAV rep and cap genes which does not carry the ITR sequences and further comprising adenoviral helper genes.

In a further particular embodiment, optionally in combination with one or more features of the various embodiments described above or below, the host cell comprises:
 a) a nucleic acid construct or an expression vector of the invention (i.e., the recombinant AAV genome);
 b) a plasmid encoding AAV rep and cap genes which does not carry the ITR sequences; and
 c) a plasmid comprising adenoviral helper genes E2a, E4, and VA RNAs;
wherein co-transfection is performed in cells, preferably mammalian cells, that constitutively express and trans-complement the adenoviral E1 gene, like HEK-293 cells (ATCC CRL-1573).

Large-scale production of AAV vectors according to the invention can also be carried out for example by infection of insect cells with a combination of recombinant baculoviruses (Urabe et al. *Hum. Gene Ther.* 2002; 13: 1935-1943). SF9 cells are co-infected with three baculovirus vectors respectively expressing AAV rep, AAV cap and the AAV vector to be packaged. The recombinant baculovirus vectors will provide the viral helper gene functions required for virus replication and/or packaging.

By using helper plasmids encoding the rep ORF (open reading frame) of an AAV serotype and cap ORF of a different serotype AAV, it is feasible packaging a vector flanked by ITRs of a given AAV serotype into virions assembled from capsid structural proteins of a different serotype. It is also possible by this same procedure packaging mosaic, chimeric or targeted vectors.

On the other hand, the production of HC-Ad vectors according to the invention can be carried out by means of mammalian cells that constitutively express and trans-complement the adenoviral E1 gene, and also Cre recombinase (e.g. 293Cre cells). These cells are transfected with the HC-Ad vector genome and infected with a first-generation adenoviral helper virus (E1-deleted) in which the packaging signal is flanked by loxP sequences. [Parks R J et al. *Proc. Natl. Acad. Sci. USA* 1996; 13565-13570; for 293Cre cells, see Palmer and Engel. *Mol. Ther.* 2003; 8:846-852]. Several Cre/loxP-based helper virus systems have been described that can be used for packaging HC-Ad vectors, such as AdAdLC8cluc, or the optimized self-inactivating AdTetCre helper virus (EP2295591; Gonzalez-Aparicio et al. *Gene Therapy* 2011; 18: 1025-1033).

Further guidance for the construction and production of viral vectors for gene therapy according to the invention can be found in:

Viral Vectors for Gene Therapy, Methods and Protocols. Series: Methods in Molecular Biology, Vol. 737. Merten and Al-Rubeai (Eds.); 2011 Humana Press (Springer).

Gene Therapy. M. Giacca. 2010 Springer-Verlag.

Heilbronn R. and Weger S. Viral Vectors for Gene Transfer: Current Status of Gene Therapeutics. In: Drug Delivery, Handbook of Experimental Pharmacology 197; M. Schafer-Korting (Ed.). 2010 Springer-Verlag; pp. 143-170.

Adeno-Associated Virus: Methods and Protocols. R. O. Snyder and P. Moulllier (Eds). 2011 Humana Press (Springer).

Bünning H. et al. Recent developments in adeno-associated virus technology. J. Gene Med. 2008; 10:717-733.

Adenovirus: Methods and Protocols. M. Chillón and A. Bosch (Eds.); Third. Edition. 2014 Humana Press (Springer).

Therapeutic Uses

In a further aspect, the invention relates to the product of the invention as defined within the Summary of the invention for use as a medicament.

In an additional aspect, the invention relates to the product of the invention as defined within the Summary of the invention for use in the treatment of a condition caused by a deficiency or dysfunction of Copper-transporting ATPase 2, and of any other conditions and illnesses in which an upregulation of Copper-transporting ATPase 2 expression and activity may produce a therapeutic benefit or improvement, in particular a disease or condition associated with a decrease of ATP7B-dependent lysosomal exocytosis and accumulation of copper in lysosomes, such as choleostatic disorders, Alzheimer disease and/or cancer (Polishchuck et al. Dev Cell. 2014, 29(6), 686-700; Gupta and Lutsenko, Future Med. Chem. 2009, 1, 1125-1142).

The subject to be treated can be a mammal, and in particular a human patient.

In a particular embodiment, optionally in combination with one or more features of the various embodiments described above or below, the condition caused by a deficiency or dysfunction of Copper-transporting ATPase is Wilson's disease (WD, Online Mendelian Inheritance in Man catalog accession number OMIN 277900).

In a related aspect, the invention pertains to the use of the product of the invention, as defined within the Summary of the invention, in the preparation of a medicament for use in the treatment of a condition caused by a deficiency or dysfunction of Copper-transporting ATPase 2, and of any other conditions and illnesses in which an upregulation of Copper-transporting ATPase 2 expression and activity may produce a therapeutic benefit or improvement, preferably for use in the treatment of Wilson's disease.

In a further aspect, the invention relates to the treatment of a condition caused by a deficiency or dysfunction of Copper-transporting ATPase 2, and of any other conditions and illnesses in which an upregulation of Copper-transporting ATPase 2 expression and activity may produce a therapeutic benefit or improvement, preferably for use in the treatment of Wilson's disease, in a patient that comprises administering to the patient a therapeutically effective amount of a nucleic acid construct, an expression vector, a host cell, a viral particle or a pharmaceutical composition of the invention. The treatment with a product of the invention may alleviate, ameliorate, or reduce the severity of one or more symptoms of WD. For example, treatment may increase and/or restore holoceruplasmin synthesis, ceruloplasmin oxidase activity, and/or copper excretion in the bile (thus reducing copper accumulation in serum, liver, brain and urine); and as a consequence may alleviate, ameliorate, or reduce the severity of abdominal pain, fatigue, jaundice, frequency of uncontrolled movements, muscle stiffness, problems with speech, swallowing or physical coordination.

The product of the invention will be typically included in a pharmaceutical composition or medicament, optionally in combination with a pharmaceutical carrier, diluent and/or adjuvant. Such composition or medicinal product comprises the product of the invention in an effective amount, sufficient to provide a desired therapeutic effect, and a pharmaceutically acceptable carrier or excipient.

Accordingly, in a further aspect, the invention relates to a pharmaceutical composition that comprises a nucleic acid construct, an expression vector, a host cell or a viral particle of the invention, and a pharmaceutically acceptable carrier.

Any suitable pharmaceutically acceptable carrier or excipient can be used in the preparation of a pharmaceutical composition according to the invention (See e.g., Remington: The Science and Practice of Pharmacy, Alfonso R. Gennaro (Editor) Mack Publishing Company, April 1997). Pharmaceutical compositions are typically sterile and stable under the conditions of manufacture and storage. Pharmaceutical compositions may be formulated as solutions (e.g. saline, dextrose solution, or buffered solution, or other pharmaceutically acceptable sterile fluids), microemulsions, liposomes, or other ordered structure suitable to accommodate a high product concentration (e.g. microparticles or nanoparticles). The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The product of the invention may be administered in a controlled release formulation, for example in a composition which includes a slow release polymer or other carriers that protect the product against rapid release, including implants and microencapsulated delivery systems. Biodegradable and biocompatible polymers may for example be used, such as ethylene vinyl acetate, polyanhydrides, polyglycolic acid, collagen, polyorthoesters, polylactic acid and polylactic/polyglycolic copolymers (PLG). Preferably, said pharmaceutical composition is formulated as a solution, more preferably as an optionally buffered saline solution.

Supplementary active compounds can also be incorporated into the pharmaceutical compositions of the invention. Guidance on co-administration of additional therapeutics can for example be found in the Compendium of Pharmaceutical and Specialties (CPS) of the Canadian Pharmacists Association.

In one embodiment, optionally in combination with one or more features of the various embodiments described above or below, the pharmaceutical composition of the invention is a parenteral pharmaceutical composition, including a composition suitable for intravenous, intraarterial, subcutaneous, intraperitoneal or intramuscular administration. These pharmaceutical compositions are exemplary only and do not limit the pharmaceutical compositions suitable for other parenteral and non-parenteral administration routes.

In the context of the invention, an "effective amount" means a therapeutically effective amount.

As used herein a "therapeutically effective amount" refers to an amount effective, at dosages and for periods of time necessary to achieve the desired therapeutic result, such as an elevation of copper translocation activity, thus increasing copper in bile and reducing copper in serum, liver, brain and urine. The therapeutically effective amount of the product of the invention, or pharmaceutical composition that comprises it may vary according to factors such as the disease state, age, sex, and weight of the individual, and the ability of the product or pharmaceutical composition to elicit a desired response in the individual. Dosage regimens may be adjusted to provide the optimum therapeutic response. A therapeutically effective amount is also typically one in which any toxic or detrimental effect of the product or pharmaceutical composition is outweighed by the therapeutically beneficial effects.

In one embodiment, optionally in combination with one or more features of the various embodiments described above or below, the pharmaceutical composition carrying the product of the invention is administered to the subject or patient by a parenteral route.

In one embodiment, optionally in combination with one or more features of the various embodiments described above or below, the pharmaceutical composition is administered by intravenous, intraarterial, subcutaneous, intraperitoneal, or intramuscular route.

In one embodiment, optionally in combination with one or more features of the various embodiments described above or below, the pharmaceutical composition comprising a product of the invention is administered by interstitial route, i.e. by injection to or into the interstices of a tissue. The tissue target may be specific, for example the liver tissue, or it may be a combination of several tissues, for example the muscle and liver tissues. Exemplary tissue targets may include liver, skeletal muscle, heart muscle, adipose deposits, kidney, lung, vascular endothelium, epithelial and/or hematopoietic cells. In a preferred embodiment, optionally in combination with one or more features of the various embodiments described above or below, it is administered by intrahepatic injection, i.e. injection into the interstitial space of hepatic tissue.

The amount of product of the invention that is administered to the subject or patient may vary depending on the particular circumstances of the individual subject/patient including, age, sex, and weight of the individual; the nature and stage of the disease, the aggressiveness of the disease; the route of administration; and/or concomitant medication that has been prescribed to the subject or patient. Dosage regimens may be adjusted to provide the optimum therapeutic response.

For any particular subject, specific dosage regimens may be adjusted over time according to the individual needs and the professional judgment of the person administering or supervising the administration of the compositions. Dosage ranges set forth herein are exemplary only and do not limit the dosage ranges that may be selected by medical practitioners.

In one embodiment, an AAV vector according to the invention can be administered to the patient for the treatment of Wilson's disease in an amount or dose comprised within a range of $5 \times 10^{11}$ to $1 \times 10^{14}$ vg/kg (vg: viral genomes; kg: subject's or patient's body weight). In a more particular embodiment, the AAV vector is administered in an amount comprised within a range of $1 \times 10^{12}$ to $1 \times 10^{13}$ vg/kg.

In another embodiment, a HC-Ad vector according to the invention can be administered to the patient for the treatment of Wilson's disease in an amount or dose comprised within a range of $1 \times 10^{9}$ to $1 \times 10^{11}$ iu/kg (iu: infective units of the vector).

In another aspect, the invention further relates to a kit comprising a nucleic acid construct, vector, host cell, viral particle or pharmaceutical composition of the invention in one or more containers. A kit of the invention may include instructions or packaging materials that describe how to administer a nucleic acid construct, vector, host cell or viral particle of the invention contained within the kit to a patient. Containers of the kit can be of any suitable material, e.g., glass, plastic, metal, etc., and of any suitable size, shape, or configuration. In certain embodiments, the kits may include one or more ampoules or syringes that contain a nucleic acid construct, vector, host cell, viral particle or pharmaceutical composition of the invention in a suitable liquid or solution form.

Throughout the description and claims the word "comprise" and variations of thereof, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1. Construction of Recombinant Expression Vectors

Two different AAV vectors that carry and express human ATP7B were designed and produced for gene therapy of Wilson's Disease (WD): AAV2/8-AAT-wtATP7B and AAV2/8-AAT-coATP7B.

1.1 Vector AAV2/8-AAT-wtATP7B

Firstly, the plasmid pUC-ATP7B was assembled at request (GenScript) by cloning nucleic acid construct into a pUC57 plasmid. Nucleic acid construct contained cDNA sequence encoding human ATP7B (transgene) together with a synthetic polyadenylation signal sequence (Levitt N. et al. *Genes & Development* 1989; 3(7):1019-1025) downstream of the transgene.

Next, the minimal promoter of alpha1 anti-trypsin gene (AAT) was introduced into the plasmid pUC-ATP7B, upstream the ATP7B gene. The minimal promoter consists on the sequence from nucleotide −261 to nucleotide+44 relative to cap site of the AAT promoter (Kramer M. G. et al. *Mol. Therapy* 2003; 7(3): 375-385) and contains the tissue-specific element (TSE), required for liver function, and the distal region (DRI) required for whole promoter activity. The AAT promoter was obtained by PCR amplification using as template the pEnhAlbAAT-luciferase plasmid (provided by M. G. Kramer) and the following primers:

```
Primer AAT-Forward
                                    (SEQ. ID. NO. 5)
5' CTGGTCTAGAACGCGTCGCCACCCCCTCCACCTTGG 3';
and (SEQ. ID. NO. 6)
Primer AAT-reverse
5' ATCATGATGCGGCCGCTTCACTGTCCCAGGTCAGTG 3'.
```

The AAT-Forward primer has a restriction site for XbaI and MluI and the AAT-reverse primer has a restriction site for NotI.

Therefore, in order to obtain plasmid pUC-AAT-ATP7B, the plasmid pUC-ATP7B was digested with XbaI and NotI and ligated to AAT promoter previously digested with the same enzymes.

The expression cassette was subsequently subcloned into the AAV transfer plasmid pAAV-MCS (Agilent technologies) by digestion with restriction enzymes PmlI and MluI, thus producing the plasmid pAAV2-AAT-wtATP7B (FIG. 1; SEQ.ID.NO.1).

Once the plasmid had been constructed the AAV vector was made by double transfection into 293 cells of, the plasmid pAAV2-AAT-ATP7B and plasmid pDP8 (obtained from PlasmidFactory, Bielefeld, Germany; plasmid pDP8 expresses AAV8 capsid protein, AAV2 rep protein and the adenoviral molecules required for production and packaging of AAV).

The vector was finally purified by iodixanol gradient and titrated by quantitative PCR.

1.2 Vector AAV2/8-AAT-coATP7B

To obtain the AAV vector expressing a codon optimized version of the ATP7B gene (coATP7B), the plasmid pUC-coATP7B was firstly assembled at request (GenScript) by cloning nucleic acid construct into a pUC57 plasmid. Next the coATP7B was excised from the pUC-coATP7B by digestion with the restriction enzymes NotI and KpnI and subcloned into the pAAV2-AAT-wtATP7B plasmid previously digested with the same enzymes, NotI and KpnI, to obtain the plasmid pAAV2-AAT-coATP7B (SEQ.ID.NO.2).

Once the plasmid had been constructed, their production and packaging of viral particles was performed as has been described previously for the vector AAV2/8-AAT-wtATP7B: double transfection of previously obtained plasmid pAAV2-AAT-coATP7B with plasmid pDP8, purification (iodixanol gradient) and titration.

Example 2. Wilson's Disease Animal Model: ATP7B KO

The therapeutic performance of the vector AAV2/8-AAT-wtATP7B was tested in ATP7B knockout mice (ATP7B KO, ATP7B$^{-/-}$ or WD mice) which are a representative animal model of WD. This animal model was developed by Buiakova et al., by introducing an early termination codon in the mouse ATP7B mRNA by engineering the substitution of a portion of ATP7B exon 2 with a neomycin cassette oriented in the opposite transcriptional frame (Buikova O. I. et al. *Human Molecular Genetics* 1999; 8(9): 1665-1671). ATP7B knockout mice show no ATP7B expression in the liver and high Cu excretion in the urine, low holoceruloplasmin levels in serum, high transaminase levels, high Cu concentration in the liver and a pathologic liver histology. These mice exhibit the typical biochemical characteristics of human Wilson's disease except for the neurological affectation (Lutsenko S. Biochemical Society Transactions 2008; 36(Pt 6): 1233-1238).

Example 3. Therapeutic Effect of Viral Vector AAV2/8-AAT-wtATP7B in Wilson's Disease Mice Six weeks (6 w) old male ATP7B$^{-/-}$ mice were divided in 3 groups of 5 mice each: 2 of the groups were treated intravenously with the vector AAV2/8-AAT-wtATP7B at two different doses, $1 \times 10^{10}$ vg/mouse (vg: viral genomes) and $3 \times 10^{10}$ vg/mouse respectively diluted in saline solution; third group was left untreated. An additional group of wild type mice was kept untreated as a control group. Animals were sacrificed twenty-four weeks after vector administration (w30).

Four weeks after vector administration (w10) and every five weeks up to week 30 (w15, w20, w25, and w30), serum transaminases (ALT) levels, serum ceruloplasmin activity and urine Cu content were determined in all the groups.

Serum transaminases (ALT) levels were determined by the DGKC method (Roche Diagnostics, Mannheim, Germany) using a Hitachi 747 Clinical Analyzer (Hitachi, Tokyo, Japan).

Serum ceruloplasmin activity was determined with o-dianisidine dihydrochloride (4, 4'-diamino-3,3'-dimethoxy-biphenyl) as substrate (Sigma-Aldrich, San Louis, Mo., United States) as described by Schosinsky and cols. (Clinical Chemistry 1974; 20(12): 1556-1563). Absorbance was measured at 540 nm in a spectrophotometer.

Urine copper content was determined by atomic absorption spectroscopy (SIMAA 6000, from Perkin-Elmer GmbH, Bodenseewerk).

After the sacrifice the liver was excised for histological determination and analysis of Cu content, inflammation, biliary duct proliferation and fibrosis.

Hepatic copper content was determined in dry liver tissue by atomic absorption spectroscopy (SIMAA 6000, from Perkin-Elmer GmbH, Bodenseewerk), and by Timm's sulphide silver staining (Danscher G. and Zimmer *J. Histochemistry* 1978; 55(1): 27-40).

Liver structure was assessed in sections stained with hematoxylin and eosin.

Immunohistochemistry with anti-mouse CD45 antibody (BioLegend, San Diego, USA; Catalog Number 103102) was performed to detect inflammatory infiltration in the liver.

Immunohistochemistry with anti-mouse PanCk antibody (Invitrogen/Life Technologies, 18-0132, clon AE1/AE3) was also performed to detect biliary duct cells.

To determine fibrosis conventional Sirius Red staining was used as a method for collagen determination.

To quantitatively analyze liver inflammation, bile ducts proliferation and fibrosis, digital images were acquired with an Axiolmager.MI microscope (Zeiss, Germany) using an in-house Metamorph macro (Molecular Devices, USA). This equipment allowed to capture randomly located images at 20× (Plan-Neofluar objective with 0.50 NA), with automatic focus, white balance and shadow correction, on every acquired image. All images were stored in uncompressed 24-bit color TIFF format. Images were automatically analyzed using a plugin developed for Fiji, ImageJ.41.

As shown in FIG. 2, transaminase levels were normalized in the mice receiving AAV2/8-AAT-wtATP7B, independently of the dose. As early as 4 weeks after treatment serum transaminase levels significantly decreased (FIG. 2). Furthermore, the concentration of Cu in urine was significantly lower in the animals that received the gene therapy vector (FIG. 3). Ceruloplasmin activity was restored four weeks after treatment in the animals receiving the higher dose of the vector ($3 \times 10^{10}$ vg/mouse) but not in the animals receiving the lower dose (FIG. 4).

On the other hand, the administration of the vector significantly reduced Cu content in the liver (FIG. 5A); the result was confirmed in the images obtained after Timm's staining (FIG. 6A). It is worth noticing that hepatic copper content was totally normalized in all the animals that received the higher dose of the vector AAV2/8-AAT-wtATP7B (FIG. 5B). Regarding liver histology, untreated animals showed an abnormal hepatic architecture with huge hepatocytes containing enormous nuclei. The administration of the vector resulted in the normalization of liver histology (FIG. 6B). Furthermore, Wilson's disease animals presented a strong liver infiltrate mainly composed by CD45 positive cells; infiltration disappeared after treatment with the recombinant viral vector (FIG. 7A). Biliary ducts proliferation (FIG. 7B) and liver fibrosis (FIG. 7C) were also significantly reduced. The quantitative data analysis indicated that the high and the low dose of the therapeutic virus significantly reduced bile duct proliferation and fibrosis, however only the high dose of virus normalized liver inflammation (FIG. 8).

Example 4. Effect of Viral Vector AAV2/8-AAT-wtATP7B Treatment on the Copper Metabolism of Wilson's Disease Mice To investigate whether the vector of the invention was able to restore physiological biliary copper excretion, 6 weeks-old WD mice (n=5 per group) were treated with AAV2/8-AAT-wtATP7B ($3 \times 10^{10}$ vg/mouse by intravenous route) or were left untreated, and a group of heterozygous littermates was used as control. Two weeks after treatment, half of the animals received a copper overload by intraperitoneal administration of 100 µg $CuSO_4$, ($+CuSO_4$); and the other half saline as a control ($-CuSO_4$); and were placed in a metabolic cage for urine and feces collection during 24 hours.

The copper content of urine and feces was then determined by flame atomic absorption spectrophotometry (Perkin Elmer AAnalyst 800, Norwalk, Conn., USA).

Figure 9A:
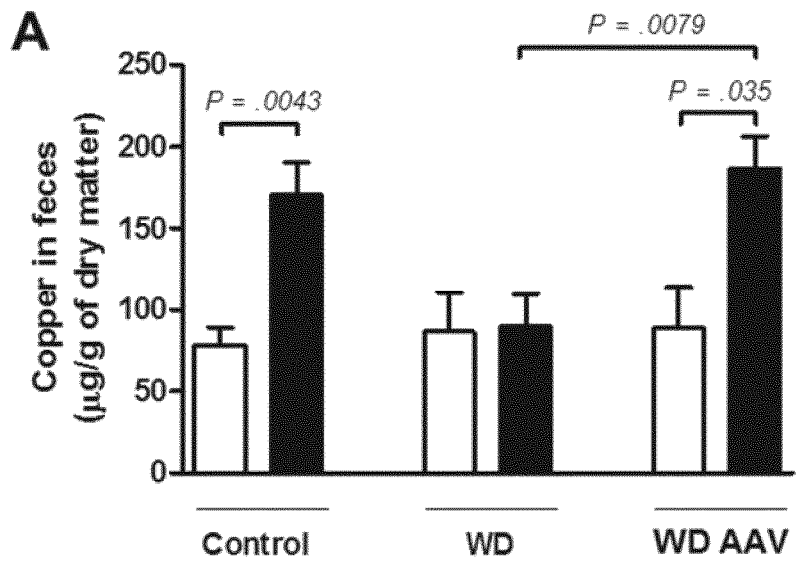
Figure 9B:
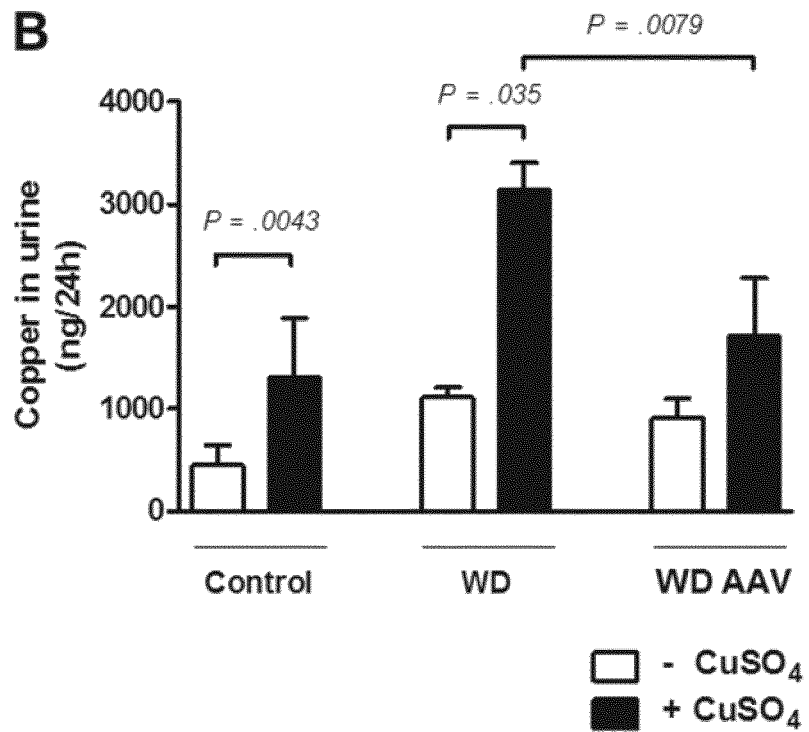

We found that WT control animals and AAV2/8-AAT-wtATP7B-treated WD mice were similarly able to excrete the excess of copper in feces (FIG. 9A). In contrast, copper overload did not change fecal copper excretion in untreated WD mice, and as a result urinary copper was significantly higher in this group compared to AAV2/8-AAT-wtATP7B-treated WD mice (FIG. 9B).

These data clearly demonstrate that AAV2/8-AAT-wtATP7B restores normal copper metabolism in WD mice.

Example 5. Therapeutic Effect of Viral Vector AAV2/8-AAT-coATP7B in Wilson's Disease Mice Six weeks (6 w) old male $ATP7B^{-/-}$ mice were divided in 3 groups of mice: the first group was treated intravenously with the vector AAV2/8-AAT-wtATP7B at suboptimal dose of $1 \times 10^{10}$ vg/mouse diluted in saline solution; the second group was treated the same way with AAV2/8-AAT-coATP7B; and the third group was left untreated. An additional group of wild type mice was kept untreated as a control group. Animals were sacrificed twenty-four weeks after vector administration (w30).

Four weeks after vector administration and every five weeks up to week 30, serum transaminases (ALT) levels, serum ceruloplasmin activity and urine Cu content were determined in all the groups. After the sacrifice of the animals the liver was excised for histological determination and analysis of Cu content.

As it is shown in FIG. 10, both AAV2/8-AAT-wtATP7B and AAV2/8-AAT-coATP7B given at a suboptimal dose reduced accumulation of copper in the liver of WD mice.

The invention claimed is:

1. A nucleic acid construct that comprises:
   a) a nucleotide sequence of the α1-antitrypsin gene (AAT) core promoter;
   b) a nucleotide sequence encoding a Copper-transporting ATPase 2;
   c) a polyadenylation signal sequence; and
   d) a 5'ITR sequence and a 3'ITR sequence of an adeno-associated virus (AAV),
   wherein the AAT core promoter is the only eukaryotic regulatory element in the nucleic acid construct.

2. The nucleic acid construct according to claim 1, wherein the nucleotide sequence of the AAT core promoter consists of nucleotides 156 through 460 of SEQ ID NO:1.

3. The nucleic acid construct according to claim 1, wherein the nucleotide sequence encoding the Copper-transporting ATPase 2 encodes the amino acid sequence of SEQ ID NO:3.

4. The nucleic acid construct according to claim 1, wherein the nucleotide sequence encoding the Copper-transporting ATPase 2 is selected from the group consisting of a) nucleotides 473 through 4870 of SEQ ID NO:1;
b) nucleotides 473 through 4870 of SEQ ID NO:2; and
c) a nucleotide sequence wherein at least 1170 of the codons encoding the Copper-transporting ATPase 2 are identical to the codons of nucleotides 473 through 4870 of SEQ ID NO:2.

5. The nucleic acid construct according to claim 1, wherein the 5'ITR sequence and the 3'ITR sequence of an AAV are of a serotype selected from the group consisting of an AAV1, an AAV2, and an AAV4.

6. The nucleic acid construct according to claim 1, wherein the construct comprises the nucleotide sequence of SEQ ID NO:1 or SEQ ID NO:2.

7. An expression vector comprising the nucleic acid construct according to claim 1.

8. The expression vector according to claim 7, wherein the vector is an AAV vector.

9. A host cell comprising a nucleic acid construct according to claim 1.

10. A viral particle that comprises a nucleic acid construct according to claim 1.

11. The viral particle according to claim 10, wherein the viral particle comprises a capsid protein of an AAV.

12. The viral particle according to claim 10, wherein the viral particle comprises a capsid protein of an AAV of a serotype selected from one or more of the group consisting of AAV1, AAV3, AAV4, AAV5, AAV6, AAV7, AAV8, AAV9, and AAV10.

13. The viral particle according to claim 12, wherein the 5' sequence and the 3'ITR sequence of the nucleic acid construct are of an AAV2 serotype and the capsid protein is of an AAV3B serotype.

14. The viral particle according of claim 12, wherein the viral particle comprises a capsid protein of an AAV of a serotype AAV3B.

15. A pharmaceutical composition comprising a pharmaceutically acceptable carrier and a nucleic acid construct according to claim 1.

16. A kit comprising:
a nucleic acid construct according to claim 1 in one or more containers; and
instructions or packaging materials that describe how to administer the nucleic acid construct to a patient.

17. A medicament comprising an AAV vector according to claim 8.

18. A pharmaceutical composition comprising a pharmaceutically acceptable carrier and the viral particle according to claim 13.

19. A viral particle comprising:
a nucleic acid construct comprising:
a) a 5'ITR sequence of an AAV2 serotype;
b) a nucleotide sequence of an AAT promoter wherein the nucleotide sequence consists of nucleotides 156 through 460 of SEQ ID NO:1 as the only eukaryotic regulatory element sequence in the nucleic acid construct;
c) a nucleotide sequence encoding a Copper-transporting ATPase 2;
d) a polyadenylation signal sequence wherein the sequence comprises nucleotides 4877 through 4932 of SEQ ID NO:1; and
e) a 3'ITR sequence of an AAV2 serotype; and
a capsid protein of AAV3B.

20. A pharmaceutical composition comprising the viral particle of claim 19, and a pharmaceutically acceptable carrier or excipient.

21. A method of treating a condition caused by a deficiency or dysfunction of Copper-transporting ATPase 2 in a patient, the method comprising administering to the patient a therapeutically effective amount of a nucleic acid construct according to claim 1.

22. The method according to claim 21, wherein the condition is Wilson's disease.

23. A process of producing a viral particle according to claim 10, comprising the steps of:
a) culturing a host cell comprising the nucleic acid construct in a culture medium; and
b) harvesting the viral particles from the cell culture supernatant and/or from the host cell,
wherein the host cell further comprises:
i) a nucleic acid construct encoding AAV rep and/or cap genes which do not comprise an ITR sequence; and/or
ii) a nucleic acid construct comprising a viral helper gene.

24. A method of treating a condition caused by a deficiency or dysfunction of Copper-transporting ATPase 2 in a patient, the method comprising administering to the patient a therapeutically effective amount of a viral particle according to claim 13.

* * * * *